United States Patent
Van Binsbergen et al.

(10) Patent No.: US 9,247,707 B2
(45) Date of Patent: Feb. 2, 2016

(54) KENTUCKY BLUEGRASS VARIETY NAMED 'BARVETTE' SELECTED FOR HEALTHY TURF

(71) Applicant: BARENBRUG USA, INC., Tangent, OR (US)

(72) Inventors: Everard Van Binsbergen, Wolfheze (NL); Devesh Singh, Albany, OR (US); Joseph K. Wipff, III, Canby, OR (US)

(73) Assignee: BARENBRUG USA, INC., Tangent, OR (US)

( * ) Notice: Subject to any disclaimer, the term of this patent is extended or adjusted under 35 U.S.C. 154(b) by 158 days.

(21) Appl. No.: 13/750,827

(22) Filed: Jan. 25, 2013

(65) Prior Publication Data

US 2014/0215651 A1 Jul. 31, 2014

(51) Int. Cl.
*A01H 5/00* (2006.01)
*A01H 5/10* (2006.01)
*A01H 5/12* (2006.01)

(52) U.S. Cl.
CPC ...................................... *A01H 5/12* (2013.01)

(58) Field of Classification Search
None
See application file for complete search history.

(56) References Cited

U.S. PATENT DOCUMENTS

| | | | |
|---|---|---|---|
| 5,304,719 | A | 4/1994 | Segebart |
| 5,367,109 | A | 11/1994 | Segebart |
| 5,523,520 | A | 6/1996 | Hunsperger et al. |
| 5,850,009 | A | 12/1998 | Kevern |
| 5,968,830 | A | 10/1999 | Dan et al. |
| 6,211,438 | B1 | 4/2001 | Anderson et al. |
| PP12,435 | P2 * | 3/2002 | Meier et al. |
| 2007/0074303 | A1 * | 3/2007 | McCutchen et al. .......... 800/278 |

OTHER PUBLICATIONS

Eshed, Y. and Zamir, D., "Less-than-additive epistatic interactions of quantitative trait loci in tomato", *Genetics*, 1996, 143:1807-1817.
Kraft, T., Hansen, M., and Nilsson, N. O., "Linkage disequilibrium and fingerprinting in sugar beet", *Theor. Appl. Genet.*, 2000, 101:323-326.
Poehlman, J.M. and Sleper, D.A., "Breeding Field Crops", 4th Edition, Iowa State University Press, 1995, pp. 172-174.
Narvel, J.M., et al., "A Retrospective DNA Marker Assessment of the Development of Insect Resistant Soybean", *Crop Science*, 2001, 41:1931-1939.
Goldman, I.L., Rocheford, T.R. and Dudley, J.W., "Molecular Markers Associated with Maize Kernel Oil Concentration in an Illinois High Protein x Illinois Low Protein Cross", *Crop Science*, 1994, 34:908-915.

* cited by examiner

*Primary Examiner* — David H Kruse
*Assistant Examiner* — Jason Deveau Rosen
(74) *Attorney, Agent, or Firm* — Jondle & Associates, P.C.

(57) ABSTRACT

The present invention is directed toward Kentucky bluegrass varieties containing mutant allele BARHGTMA1 that exhibit resistance to diseases, pests and traffic. Specifically, the Kentucky bluegrass variety of the present invention, 'Barvette', exhibits the unique and surprising combination of resistance to Summer Patch caused by the fungus *Magnaporthe poae*, traffic tolerance and recovery, increased billbug and white grub tolerance, stem rust resistance and increased tolerance to summer stresses. The invention relates to seeds, plants and plant parts of Kentucky bluegrass variety 'Barvette', and also to progeny of Kentucky bluegrass variety 'Barvette' and to methods for producing other Kentucky bluegrass plants or plant parts from 'Barvette', and to the plants and parts derived from use of those methods. The invention further relates to hybrid Kentucky bluegrass seeds, plants, and plant parts produced by crossing 'Barvette' with another Kentucky bluegrass variety, species of *Poa*, or plant genus.

25 Claims, No Drawings

US 9,247,707 B2

KENTUCKY BLUEGRASS VARIETY NAMED 'BARVETTE' SELECTED FOR HEALTHY TURF

BACKGROUND OF THE INVENTION

The present invention relates to new Kentucky bluegrass (*Poa pratensis* L.) varieties containing mutant allele BARHGTMA1 that exhibit resistance to diseases, pests and traffic, exemplified herein by Kentucky bluegrass (*Poa pratensis* L.) variety designated 'Barvette', also known as 'Barvette' with the trademark HGT. All publications cited in this application are herein incorporated by reference.

Turfgrass plays a major role in our daily life. Turfgrass, from a beautification standpoint, provides a canvas for landscaped areas contributing to aesthetic appeal and adding to economic value. Recreational facilities include an array of sports fields, golf courses, parks and lawns. Turfgrass also provides functional value including dust control, erosion control, reduced surface temperatures and glare reduction.

Use and appearance are important considerations for turfgrass. To best serve a particular function, the turf should be suitable for the use for which it is intended and aesthetically appealing. Turfgrass should also be well-adapted to the environment where it will be planted. Based on climatic adaptation, turfgrass species have been placed into four categories: adapted for cool humid regions, warm humid regions, cool arid regions, and warm arid regions. The major turfgrasses adapted to the cool humid regions, and irrigated areas of the cool arid regions, are species of *Agrostis, Poa, Festuca*, and *Lolium*. In the warm humid and irrigated areas of the warm arid regions, the major adapted turfgrasses are species of *Cynodon, Zoysia, Stenotaphrum, Eremochloa, Paspalum, Festuca*, and *Agropyron*. In the non-irrigated warm arid regions, species of *Buchloe* and *Bouteloua* are adapted.

Kentucky bluegrass (*Poa pratensis*), also called smooth meadow grass, spear grass and June grass, is a perennial species of grass native to Europe, northern Asia and the mountains of Algeria and Morocco. Although the species is spread over all of the cool, humid parts of the United States, Kentucky bluegrass is native only to the subarctic and arctic portions of North America. Kentucky bluegrass forms a valuable pasture plant, characteristic of well-drained, fertile soil, and is a popular sod-forming grass that is used on golf courses, ski slopes, campsites, gardens and lawns. Kentucky bluegrass is also an important forage species for sheep and cattle. The name Kentucky bluegrass derives from its flower heads, which are blue when the plant is allowed to grow to its natural height of two to three feet.

Since 1985, almost 600 varieties of Kentucky bluegrass have been developed and evaluated in the National Turf Evaluation Program (NTEP) in the United States alone. Some varieties tolerate southern climates better than others, some have moderate shade tolerance, and some tolerate closer mowing. Many of these grasses also differ in their degree of susceptibility to diseases. Kentucky bluegrass is distinguished from Canada bluegrass (*Poa compressa*) by its darker green foliage, longer leaves, rounded culms and pubescence at the bases of the leaves, whereas *P. compressa* has strongly compressed, flattened culms. Kentucky bluegrass can also be compared to Annual Meadowgrass (*Poa annua*) and Rough Meadowgrass (*Poa trivialis*), which have a ligule that is silvery and pointed, whereas Kentucky bluegrass has a ligule that is extremely short and square ended.

Kentucky bluegrass typically grows 18 to 36 inches tall and is readily identified by its boat-shaped leaf tip. Kentucky bluegrass spreads by rhizomes and tillers and forms a dense sod. New shoots (rhizomes and tillers) are produced primarily in the spring and late summer. Most shoots produced in the spring remain vegetative, while shoots produced in late summer often terminate in an inflorescence the following spring. The lifetime of a Kentucky bluegrass shoot that terminates in an inflorescence ends soon after the seeds mature.

Kentucky bluegrass is often included in seed mixes that are used to revegetate roadbanks Kentucky bluegrass is a slow-growing grass that establishes in 2 to 3 years and forms a dense sod. Kentucky bluegrass grows best on well-drained loams or clay loams rich in humus and on soils with limestone parent material. Kentucky bluegrass requires large amounts of nitrogen during active growth stages and has an optimal soil pH of between 6 and 7. Additionally, Kentucky bluegrass is intolerant of drought, excessive flooding, high water tables, and poorly drained soils, and is often vulnerable to fungal infections including Summer Patch caused by *Magnaporthe poae* Lanschoot & N. Jackson, *Fusarium, Helminthosporium*, leaf spot, rust and powdery mildew, as well as infestation by billbugs and white grubs.

It is therefore desirable to have Kentucky bluegrass plants that are tolerant of summer stresses, and resistant to disease, pests and traffic.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there are provided novel Kentucky bluegrass varieties, botanically known as *Poa pratensis* L., containing mutant allele BARHGTMA1, which exhibit resistance to diseases, pests and traffic. This invention thus relates to the seeds of Kentucky bluegrass varieties which exhibit resistance to diseases, pests and traffic, to the plants or part(s) thereof of Kentucky bluegrass varieties which exhibit resistance to diseases, pests and traffic, to plants or part(s) thereof having all the phenotypic and morphological characteristics of Kentucky bluegrass varieties which exhibit resistance to diseases, pests and traffic, and to methods for producing a Kentucky bluegrass plant produced by crossing Kentucky bluegrass varieties which exhibit resistance to diseases, pests and traffic with itself or another bluegrass variety, and the creation of variants by mutagenesis or transformation of Kentucky bluegrass varieties which exhibit resistance to diseases, pests and traffic.

In one embodiment of the invention, there are provided novel Kentucky bluegrass plants (*Poa pratensis* L.) containing mutant allele BARHGTMA1, which confers resistance to Summer Patch. This invention thus relates to the seeds of Kentucky bluegrass plants containing mutant allele BARHGTMA1, to the plants or part(s) thereof of Kentucky bluegrass plants containing mutant allele BARHGTMA1, to plants or part(s) thereof having the phenotypic and morphological characteristics of Kentucky bluegrass plants containing mutant allele BARHGTMA1, and to methods for producing a Kentucky bluegrass plant produced by crossing Kentucky bluegrass plants containing mutant allele BARHGTMA1 with itself or another bluegrass variety, and the creation of variants by mutagenesis or transformation of Kentucky bluegrass plants containing mutant allele BAR-HGTMA1.

In one embodiment of the invention, there is provided a novel Kentucky bluegrass variety, botanically known as *Poa pratensis* L., and herein designated 'Barvette'. This invention thus relates to the seeds of Kentucky bluegrass variety 'Barvette', to the plants or part(s) thereof of Kentucky bluegrass variety 'Barvette', to plants or part(s) thereof having all the phenotypic and morphological characteristics of Kentucky bluegrass variety 'Barvette', and to methods for producing a Kentucky bluegrass plant produced by crossing Kentucky bluegrass variety 'Barvette' with itself or another bluegrass variety, and the creation of variants by mutagenesis or transformation of Kentucky bluegrass variety 'Barvette'.

In another aspect, the present invention provides regenerable cells for use in tissue culture of Kentucky bluegrass variety 'Barvette'. The tissue culture will preferably be capable of regenerating plants having the physiological and morphological characteristics of Kentucky bluegrass variety 'Barvette'. Preferably, the cells of such tissue culture will be embryos, meristematic cells, seeds, callus, pollen, leaves, anthers, pistils, roots, root tips, pods, flowers and stems. Protoplasts produced from such tissue culture are also included in the present invention. The Kentucky bluegrass plants regenerated from the tissue culture are also part of the invention.

Also included in the invention are methods for producing a bluegrass plant produced by crossing Kentucky bluegrass variety 'Barvette' with itself or another Kentucky bluegrass variety. When crossed with itself, i.e., when crossed with another Kentucky bluegrass variety 'Barvette' plant or self-pollinated, Kentucky bluegrass variety 'Barvette' will be conserved. When crossed with another, different bluegrass plant, an $F_1$ hybrid seed is produced. $F_1$ hybrid seeds and plants produced by growing said hybrid seeds are included in the present invention. A method for producing an $F_1$ hybrid grass seed comprising crossing a Kentucky bluegrass variety 'Barvette' plant with a different bluegrass plant and harvesting the resultant hybrid bluegrass seed are also part of the invention. The hybrid bluegrass seed produced by the method comprising crossing a Kentucky bluegrass variety 'Barvette' plant with a different bluegrass plant and harvesting the resultant hybrid bluegrass seed, are included in the invention, as are the hybrid bluegrass plant or part(s) thereof, and seeds produced by growing said hybrid bluegrass seed.

In another aspect, the present invention provides transformed Kentucky bluegrass variety 'Barvette' plants or part(s) thereof that have been transformed so that its genetic material contains one or more transgenes, preferably operably linked to one or more regulatory elements. Also, the invention provides methods for producing a bluegrass plant containing in its genetic material one or more transgenes, preferably operably linked to one or more regulatory elements, by crossing a transformed Kentucky bluegrass variety 'Barvette' plant with either a second plant of another bluegrass variety, or a non-transformed Kentucky bluegrass variety 'Barvette', so that the genetic material of the progeny that results from the cross contains the transgene(s), preferably operably linked to one or more regulatory elements. The invention also provides methods for producing a bluegrass plant that contains in its genetic material one or more transgene(s), wherein the method comprises crossing the variety 'Barvette' with a second bluegrass variety of another bluegrass variety which contains one or more transgene(s) operably linked to one or more regulatory element(s) so that the genetic material of the progeny that results from the cross contains the transgene(s) operably linked to one or more regulatory element(s). Transgenic bluegrass cultivars, or part(s) thereof produced by the methods are in the scope of the present invention.

The invention further comprises methods for producing a male sterile bluegrass plant, an herbicide resistant bluegrass plant, an insect resistant bluegrass plant, a disease resistant bluegrass plant, a water stress tolerant bluegrass plant, a heat stress tolerant bluegrass plant, and a bluegrass plant with improved shelf-life. Said methods comprise transforming a bluegrass variety 'Barvette' plant with a nucleic acid molecule that confers male sterility, herbicide resistance, insect resistance, disease resistance, water stress tolerance, heat stress tolerance, or improved shelf life, respectively. The transformed bluegrass plants, or part(s) thereof, obtained from the provided methods, including a male sterile bluegrass plant, an herbicide resistant bluegrass plant, an insect resistant bluegrass plant, a disease resistant bluegrass plant, a bluegrass plant tolerant to water stress, a bluegrass plant tolerant to heat stress or a bluegrass plant with improved shelf-life are included in the present invention. For the present invention and the skilled artisan, disease is understood to be fungal diseases, viral diseases, bacterial diseases or other plant pathogenic diseases and a disease resistant plant will encompass a plant resistant to fungal, viral, bacterial and other plant pathogens.

In another aspect, the present invention provides for methods of introducing one or more desired trait(s) into bluegrass variety 'Barvette' and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance to bacterial, fungal, or viral disease, increased leaf number, improved shelf-life, and tolerance to water stress or heat stress. The gene or genes may be naturally occurring gene(s) or transgene(s) introduced through genetic engineering techniques. The method for introducing the desired trait(s) is preferably a backcrossing process making use of a series of backcrosses to bluegrass variety 'Barvette' during which the desired trait(s) is maintained by selection.

In a preferred embodiment, the present invention provides methods for increasing and producing bluegrass variety 'Barvette' seed, whether by crossing a first parent bluegrass variety plant with a second parent bluegrass variety plant and harvesting the resultant bluegrass seed, wherein both said first and second parent bluegrass variety plant are the bluegrass variety 'Barvette' or by planting a bluegrass seed of the bluegrass variety 'Barvette', growing a bluegrass variety 'Barvette' plant from said seed, controlling a self pollination of the plant where the pollen produced by a grown bluegrass variety 'Barvette' plant pollinates the ovules produced by the very same bluegrass variety 'Barvette' grown plant, and harvesting the resultant seed.

The invention further provides methods for developing Kentucky bluegrass cultivars in a bluegrass breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, bluegrass plants, and part(s) thereof produced by such breeding methods are also part of the invention.

In addition to the exemplary aspects and embodiments described above, further aspects and embodiments will become apparent by study of the following descriptions.

DETAILED DESCRIPTION OF THE INVENTION

In the description and examples that follow, a number of terms are used. In order to provide a clear and consistent understanding of the specification and claims, including the scope to be given such terms, the following definitions are provided. If no definition is provided, all other technical and scientific terms used herein have the same meaning as is commonly understood by one of skill in the art to which the invention belongs.

Allele. An allele is any of one or more forms of a gene which relate to one trait or characteristic. In a diploid cell or organism, the two alleles of a given gene occupy corresponding loci on a pair of homologous chromosomes.

Alter. Alter refers to the utilization of up-regulation, down-regulation, or gene silencing.

Apomictic. As used herein, "apomictic" describes a plant that reproduces using apomixis.

Apomixis. Asexual reproduction in organisms that are also able to reproduce sexually, in which embryos are formed without fertilization or the creation of specialized reproductive cells.

Backcrossing. Backcrossing is a process in which a breeder repeatedly crosses hybrid progeny back to one of the parents, for example, a first generation hybrid $F_1$ with one of the parental genotypes of the $F_1$ hybrid.

BARHGTMA1. Refers to the mutant allele of the present invention which confers resistance to Summer Patch. A representative sample of said mutant allele has been deposited under NCIMB Number 42095.

Billbugs (Sphenophorus parvulus). A type of weevil or 'snout beetle' that damages cool season turfgrass by feeding below ground and damaging the roots or the growing crown area of the plant. Billbugs are some of the most difficult turfgrass insects to control because the adults' armor-like bodies do not readily absorb insecticides and the larvae bore inside grass stems for much of their lives.

Canopy density. As used herein, refers to the percentage of soil surface covered by the canopy of the turf.

Cell. Cell as used herein includes a plant cell, whether isolated, in tissue culture or incorporated in a plant or plant part.

Commercial Kentucky bluegrass. A commercial Kentucky bluegrass is one which has been sold commercially.

Cotyledon. A cotyledon is a seed leaf.

Crossbreeding. As used herein, "crossbreeding" refers to the act of mating (crossing) individuals of different species or varieties of plants to produce hybrids.

Crown. The crown in grass is the area at which top growth and root growth originate.

Culm. The culm is the main aerial shoot to which leaves and inflorescences are attached. The culm is a rounded or slightly flattened stem with one or more solid joints known as nodes. The leaves are attached at the nodes and if the stem is not simple but branched, branches arise only at nodes. Roots may also develop from a node where the node comes into contact with the ground (as in decumbent and prostrate stems).

Embryo. The embryo is the small plant contained within a mature seed.

Endophyte. The term endophyte is applied to fungi which live symbiotically within plant tissues for all or part of their lifecycle and cause no apparent infections.

Gene. As used herein, "gene" refers to a segment of nucleic acid. A gene can be introduced into a genome of a species, whether from a different species or from the same species, using transformation or various breeding methods.

Gene Silencing. The interruption or suppression of the expression of a gene at the level of transcription or translation.

Genotype. Refers to the genetic constitution of a cell or organism.

Grass flower or inflorescence. Flowers of grasses are borne in an inflorescence or flower head which terminates the culm and other branches of the stem. Smaller units of the inflorescence are called spikelets and these are arranged on one or more branches in a wide variety of different ways to which the standard terminology for inflorescences can be applied, but using the spikelet instead of the individual flower.

Growing season. As used herein, 'growing season' refers to the time of year during which bluegrass is actively growing, which is typically spring through fall.

HGT. HGT is a trademark that stands for Healthy Grass Technology, a tough and disease resistant Kentucky bluegrass. Kentucky bluegrass variety 'Barvette' is HGT.

Hybrid. Heterozygous offspring of two parents that differ in one or more inheritable characteristics.

Hypocotyl. A hypocotyl is the portion of an embryo or seedling between the cotyledons and the root. Therefore, it can be considered a transition zone between shoot and root.

Increased tolerance. As used herein, refers to the increased ability of a variety such as 'Barvette' to tolerate a biotic or abiotic stress/condition when compared to a different variety's ability to tolerate the same stress/condition.

Internode. The internodes act as spacers that distance one node from another.

Intercalary meristem. Intercalary meristem is a meristem at the base of the internode in monocot stems (particularly grass stems).

Julian heading days. Refers to the day-of-year number, or ordinal date, in the Gregorian calendar. For example, January $1^{st}$ is day 1 and December $31^{st}$ is day 365. Scoring of days to heading is defined as the duration from January $1^{st}$ to emergence of the first 25% of the panicles from their sheaths.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Living cover, living ground cover, percent living cover or percent cover. Refers to the amount of living turfgrass canopy in a given surface area, often expressed as a percent of the area.

Mature sod. Means sod that is 8 to 14 months old after seeding, wherein sod is mature at 8 to 11 months old after a fall seeding and sod is mature at 12 to 14 months old after a spring seeding.

Node. A node in a grass stem is a solid point at which the intercalary meristem is located. The node also contains the bud that is capable of producing a new shoot. The terminal node contains the bud that produces the inflorescence.

Pedigree Distance. Pedigree distance refers to the relationship among generations based on their ancestral links as evidenced in pedigrees. Pedigree distance may be measured by the distance of the pedigree from a given starting point in the ancestry.

Percent Identity. Percent identity as used herein refers to the comparison of the homozygous alleles of two perennial bluegrass varieties. Percent identity is determined by comparing a statistically significant number of the homozygous alleles of two developed varieties. For example, a percent identity of 90% between perennial bluegrass variety 1 and perennial bluegrass variety 2 means that the two varieties have the same allele at 90% of their loci.

Percent Similarity. Percent similarity as used herein refers to the comparison of the homozygous alleles of one perennial bluegrass variety with another bluegrass plant, and if the homozygous allele of the first bluegrass matches at least one of the alleles from the other plant then they are scored as similar. Percent similarity is determined by comparing a statistically significant number of loci and recording the number of loci with similar alleles as a percentage. A percent similarity of 90% between the first bluegrass and another plant means that the first bluegrass matches at least one of the alleles of the other plant at 90% of the loci.

Plant. As used herein, the term "plant" includes reference to an immature or mature whole plant, including a plant from which seed, roots or leaves have been removed. Seed or embryo that will produce the plant is also considered to be the plant.

Plant Height. The length of the grass plant measured from the soil surface to the tip of the inflorescence.

Plant Parts. As used herein, the term "plant parts" (or a perennial bluegrass plant, or a part thereof) includes protoplasts, leaves, stems, roots, root tips, anthers, pistils, seed, embryo, pollen, ovules, cotyledon, hypocotyl, flower, shoot, tissue, petiole, cells, meristematic cells and the like.

Primary tillers. Primary tillers are shoots arising at the crown.

Quantitative Trait Loci (QTL). Quantitative trait loci (QTL) refer to genetic loci that control to some degree numerically representable traits that are usually continuously distributed.

Recovery. As used herein, "recovery" or "traffic recovery" refers to the ability of turfgrass to increase the percent green, live cover or percent living ground cover after exposure to traffic, in other words, to fill in the damaged turf with living turf after damage. "Increased recovery" and "increased traffic recovery" refer to the ability of 'Barvette' to achieve a higher percent ground cover, up to 100%, when compared to commercial bluegrass cultivars after exposure to traffic.

Reduced damage. As used herein, refers to a decreased amount of damage inflicted, such as that from traffic or a traffic simulator, to 'Barvette' when compared to commercial Kentucky bluegrass varieties in similar environments.

Regeneration. Regeneration refers to the development of a plant from tissue culture.

Resistance. As used herein, refers to the ability of a plant to withstand the deleterious effects of particular diseases, pests, or stresses, such as traffic or traffic simulation. "Increased resistance" refers to an increased ability of a plant to withstand deleterious effects of particular diseases, pests, or stresses, such as traffic or traffic simulation, when compared to a commercial variety.

Rhizome. A rhizome is a modified stem that grows underground Rhizomes are jointed (thus distinguishable from roots) with bladeless leaves (scales) arising from the joints Rhizomes enable a grass plant to spread horizontally as new culms develop vertically from the joints. Thus, grasses with extensive rhizome development will form a turf rather than distinct tufts or bunches.

Secondary tillers. Secondary tillers are tillers arising as branches of the primary tillers.

Single gene converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

Single sequence repeats (SSR). Also referred to as microsatellites, SSR markers are short sequences of nucleotides that are repeated in tandem. SSRs are very polymorphic due to high mutation rates affecting the number of repeat units and the polymorphisms can easily be detected on high resolution gels by running PCR amplified fragments obtained using a unique pair of primers flanking the repeat. SSRs allow the identification of many alleles at a single locus.

Stem rust. Caused by the fungus *Puccinia graminis*, is a serious disease of turfgrass that attacks the parts of the plant that are above ground.

Stolon. A stolon is a stem that creeps across the surface of the ground, and is really a basal branch of the culm that will develop roots and shoots from some or all of its nodes. Like a rhizome, a stolon results in a spreading or turf forming grass plant.

Summer Patch. A destructive disease of Kentucky bluegrass caused by the fungus *Magnaporthe poae*, which infects and destroys roots.

Summer stress. Summer is the most stressful time of year for cool season grasses, such as Kentucky bluegrass. Summer stress is an interrelationship between heat stress and water stress. The combination of high temperatures, high humidity, and dry soils will often lead to significant declines in quality and losses in cool season turfgrasses. Specifically, but not limited to, the thinning of canopy is due to tiller and plant death and reduced growth, resulting in the weakening of turf and making the turf more susceptible to biotic stresses, such as pathogens.

Tensile strength. Means the amount of force in pounds required to tear a piece of sod in two. Tensile strength is determined with a mechanical sod stretcher coupled to a device to measure force in pounds. Tensile strength, tear point and sod strength are used interchangeably.

Tiller. A tiller is another name for a grass stem.

Tiller length. Tiller length is measured in centimeters from the lowest node to the last node subtending the green foliage.

Tolerance. The ability of a variety such as 'Barvette' to tolerate a biotic or abiotic stress/condition.

Traffic. As used herein, "traffic" or "wear" refers to any kind of movement over turfgrass, or pressure applied to turfgrass, especially by foot, athletic play, vehicles, or artificially applied by a traffic simulator, resulting in damage to the turfgrass.

Traffic simulator. Machines used to create (replicate) the traffic stresses created on turfgrass by natural athletic play. Successful simulated traffic should encompass the following parameters: 1) be uniform and reproducible; 2) the injury to the turfgrass should be similar to natural wear; and 3) the rate of the artificial, simulated wear should be accelerated greatly over the natural rate of wear in order to keep the relative number of simulated passes to a minimum.

Traffic tolerance. Also referred to as "wear tolerance". Refers to the ability of turfgrass to withstand damage from traffic, whether natural traffic or from a traffic simulator.

Transgene. A gene that is transferred from an organism of one species to an organism of another species by genetic engineering.

Turfgrass. Any of the various grasses, such as Kentucky bluegrass or perennial ryegrass, grown to form turf. Turf is a surface layer of earth containing a dense growth of grass and its matted roots; also called sod.

Variety. A taxonomic subdivision of a species consisting of naturally occurring or selectively bred populations or individuals that differ from the remainder of the species in certain minor characteristics. Used interchangeably with the term cultivar to denote a group of individuals that are distinct genetically from other groups of individuals in the same species.

Vernalization. Vernalization induces plants to begin the reproductive cycle after exposure to cold temperatures and short day length. The amount of cold exposure and short day lengths required varies with the species.

Wear. Also referred to as "traffic"; see "traffic".

Wear simulator. See "traffic simulator".

Wear tolerance. Refers to the ability of turfgrass to withstand traffic; see "traffic tolerance".

White grubs. Destructive insect pests of turfgrasses. Turfgrass is damaged throughout the summer when the grubs (the larval or immature stages of certain beetles) chew off the grass roots just below the soil surface and the resulting root injury reduces the turf's ability to take up water and nutrients and withstand the stress of hot, dry weather conditions. Many species of white grubs can cause this damage, including but not limited to the larvae of masked chafers, Japanese beetles, green June beetles, May beetles and black turfgrass *Ataenius* beetle. Control of various white grubs has become increasingly difficult since the loss of persistent chlorinated hydrocarbon insecticides.

The following detailed description is of the currently contemplated modes of carrying out the invention. The description is not to be taken in a limiting sense, but is made merely for the purpose of illustrating the general principles of the invention, since the scope of the invention is best defined by the appended claims.

Broadly, the present invention is directed toward Kentucky bluegrass varieties containing mutant allele BARHGTMA1 that exhibit resistance to diseases, pests and traffic, including both plants and seeds. Specifically, the Kentucky bluegrass variety of the present invention, 'Barvette', exhibits the unique and surprising combination of resistance to Summer Patch caused by the fungus *Magnaporthe poae*, exceptional traffic tolerance and traffic recovery, billbug tolerance, increased white grub tolerance, stem rust resistance and increased tolerance to summer stresses. The Kentucky bluegrass variety exemplified in the present invention, 'Barvette', is thus different from all known varieties of Kentucky bluegrass. Particularly, mature 'Barvette' plants reach a height from about 71 cm to about 76 cm, have a panicle length of about 11 cm long, and have a flag leaf height from about 36 cm to about 43 cm. In turf situations, the Kentucky bluegrass variety 'Barvette' forms a dense, high quality turf that has high traffic resistance and a high recovery rate from intense traffic, as well as high summer patch resistance, leaf spot, billbug and stem rust resistance, and good summer performance. Additionally, 'Barvette' establishes quickly and has exceptional spring green-up, making it ideal for sod farms, golf courses, sports fields, landscapes and lawns.

The present invention relates to a new and distinct Kentucky bluegrass grass plant designated 'Barvette' (also known as BAR VV 0709) and botanically known as *Poa pratensis* L. This new Kentucky bluegrass was developed from a research germplasm collection, designated as PP SO4, which originated from a single plant selection from a cross with many collections (~100) made in Italy in 1996. The Italian collection (PP SO4) was cloned and placed into a space plant crossing nursery in Mas Grenier, France. In 1997, PP SO4 was crossed with the other collections from Italy. The hybrid seed was harvested, sent to The Netherlands, and seeded into a turf trial. The turf was subjected to intense traffic applications. In 2000, a single, clonal patch was identified in the PP SO4 cross for its superior traffic tolerance, and designated as BAR VV 0709. In the fall of 2000, the selection, designated BAR VV 0709, was cloned into 27 plants and was established in a space plant seed increase nursery. In 2001, seed was harvested from 26 of the 27 plants, yielding a total of 400 grams. Seed was then sent from The Netherlands to the USA, and established for further evaluation in turf and wear machine trials in Illinois and Virginia. Due to BAR VV 0709's superior traffic tolerance and good turf quality, it was selected from the trial and designated for seed increase in the USA. In 2004, a 7,632 space plant nursery was established in Boardman, Oreg. and in 2005, plants were harvested and the seed was designated as BAR VV 0709. In 2005, BAR VV 0709 was entered in the National Turfgrass Evaluation Trial (NTEP) for Kentucky bluegrass and was rated top for at least six traits. The plant selection known as BAR VV 0709 had superior performance for traffic tolerance and recovery from intense traffic events; was found to be resistant to the most devastating and destructive fungal disease in Kentucky bluegrass called 'Summer Patch' caused by the fungus *Magnaporthe poae*, which infects and destroys the roots; billbug (*Sphenophorus* spp.) grub resistance; reduced damage by white grubs (e.g. *Ataenius spretulus, Popilla japonica, Cyclocephala* spp., *Phyllophaga* spp.); high stem rust resistance caused by the fungus *Puccinia graminis*; and excellent tolerances to summer stresses. The present invention has been found to be stable and reproduce true to type through successive asexual, aposporous apomixis, propagations.

Summer Patch disease in Kentucky bluegrass is caused by the pathogen *Magnaporthe poae*. Summer Patch is considered one of the most destructive diseases in turfgrass in North America and perhaps the most destructive disease of Kentucky bluegrass. The pathogen attacks and colonizes roots and crowns during periods of environmental stress and limited root growth. The infection-impaired roots cannot keep plants alive during periods of heat and drought stress. As a result, infected plants often die, leaving patches of dead turf. The pathogen is believed to survive adverse conditions as mycelium in plant debris or living host tissues.

As its name indicates, Summer Patch is a disease of hot weather and symptoms usually are present between July and September. Summer Patch is active during the summer, when turfgrass roots grow very slowly. Summer patch is most severe in areas that are poorly drained and subjected to heat and drought stress. Summer patch can be particularly severe on golf greens containing moderate to high proportions of annual bluegrass, and turf killed in midsummer adversely affects playability and ruins turf's aesthetic appearance. In turf stands where the disease has been established for several years, the infected areas have field patterns that resemble frog eye patches or arcs and rings of damaged turf.

Summer patch can be managed by selecting varieties with improved resistance and by improving cultural practices that reduce soil inoculum. There is much variation between Kentucky bluegrass varieties for resistance to Summer Patch, demonstrating that genetic resistance is achievable through plant breeding. Though currently known varieties are very limited in their resistance to Summer Patch, 'Barvette' has shown superior resistance to Summer Patch compared to other varieties in all the sites in which it has been tested. No other variety tested, other than 'Barvette', demonstrated consistent resistance across all trial sites. Though the genetic mechanism for resistance is unknown, 'Barvette' has a unique combination of genes and alleles making it extremely Summer Patch resistant. This unique genetic background may contain, but is not limited to, 1) a unique genetic make-up of genes and alleles, 2) possible new genes and alleles not observed before and 3) new mutant genes/alleles that are providing this unique and superior resistance to Summer Patch.

Not only does 'Barvette' contain a unique and novel genetic makeup, including novel genes and alleles for Summer Patch resistance, 'Barvette' may also be genetically superior in its symbiotic abilities as a host with *Lysobacter enzymogenes* C3. The role of clp-regulated factors in antagonism against *Magnaporthe poae* and biological control of Summer Patch disease of Kentucky bluegrass by *Lysobacter enzymogenes* C3 has been well documented. The symbiotic relationship with *Lysobacter enzymogenes* C3 could be enhanced by the unique genetic makeup of 'Barvette'. A clp gene homologue belonging to the crp gene family was found to globally regulate enzyme production, antimicrobial activity, and biological control activity expressed by *Lysobacter enzymogenes* C3. *L. enzymogenes* strain C3 produces numerous extracellular enzymes that contribute to biocontrol activity, including multiple forms of β-1,3-glucanases and chitinases, and also has been demonstrated to induce systemic resistance in certain plants, protecting them from pathogen infection. In addition, recent studies have indicated important roles for secondary metabolites with antibiotic activity and biosurfactant activity in fungal antagonism; several of these traits are globally controlled by a regulator encoded by the clp gene. This biocontrol range of *L. enzymogenes* C3 includes the Summer Patch disease caused by *Magnaporthe poae*. The unique genetic makeup of 'Barvette' may enhance the symbiotic relationship between it and *Lysobacter enzymogenes* C3 making 'Barvette' a superior host to the bacteria and so, enhancing the production of antagonistic enzymes that control Summer Patch disease.

The exemplary and unique trait of Summer Patch resistance exhibited by Kentucky bluegrass variety 'Barvette' may be conferred by a mutant allele designated BARHGTMA1. The allele(s) may be single genetic mutation, a single mutation with modifiers, dominant or recessive alleles, or others. The allele(s) conferring the unique traits of the present invention may be linked or isolated. Additional genetic and molecular testing will determine the mutant allele(s) of the present invention.

Kentucky bluegrass variety 'Barvette' has the following morphologic and other characteristics (based primarily on data collected at Albany, Oreg. during the 2006 to 2007 growing seasons).

TABLE 1

VARIETY DESCRIPTION INFORMATION

Classification:

| | |
|---|---|
| Family: | Poaceae |
| Botanical: | *Poa pratensis* |
| Common name: | Kentucky bluegrass |
| Experimental name: | BAR VV 0709 |
| Variety name: | 'Barvette' |
| Heading date (Julian Days): | 111 to 123 days |
| Height: | 71.3 cm to 76.0 cm |
| Flag leaf height: | 36.6 cm to 43.1 cm |
| Panicle length: | 11.2 cm to 11.3 cm |
| Flag leaf blade: | |
| Length: | 5.3 cm to 5.8 cm |
| Width: | 3.5 mm to 4.3 mm |

TABLE 1-continued

VARIETY DESCRIPTION INFORMATION

Disease and Insect resistance:

| | |
|---|---|
| Summer Patch: | Resistant |
| Billbugs: | Resistant |
| White grubs: | Highly resistant |
| Stem rust: | Resistant |
| Environmental resistance: | |
| Heat: | Tolerant |
| Drought: | Tolerant |
| Excessive traffic: | Tolerant |

It should be understood, of course, that the foregoing relates to exemplary embodiments of the invention and that modifications may be made without departing from the spirit and scope of the invention as set forth in the following claims.

Further Embodiments of the Invention

Choice of breeding or selection methods depends on the mode of plant reproduction, the heritability of the trait(s) being improved, and the type of cultivar used commercially (e.g., $F_1$ hybrid cultivar, pureline cultivar, etc.). Popular selection methods commonly include population formation by hybridization, genomic selection, marker assisted selection, recurrent selection, mutation breeding, single-seed descent, bulk selection, pedigree selection, modified pedigree selection, and mass selection.

Breeding Methods

The following describes breeding methods that may be used with bluegrass variety 'Barvette' in the development of further bluegrass plants. One such embodiment is a method for developing a cultivar 'Barvette' progeny bluegrass plant in a bluegrass plant breeding program comprising: obtaining the bluegrass plant, or a part thereof, of cultivar 'Barvette' utilizing said plant or plant part as a source of breeding material and selecting a bluegrass cultivar 'Barvette' progeny plant with molecular markers in common with variety 'Barvette' and/or with morphological and/or physiological characteristics described herein.

Another method involves producing a population of bluegrass variety 'Barvette' progeny bluegrass plants, comprising crossing cultivar 'Barvette' with another bluegrass plant, thereby producing a population of bluegrass plants, which, on average, derive 50% of their alleles from bluegrass variety 'Barvette'. A plant of this population may be selected and repeatedly selfed or sibbed with a bluegrass cultivar resulting from these successive filial generations. In some embodiments, the bluegrass cultivar produced by this method and that has obtained at least 50% of its alleles from bluegrass variety 'Barvette'.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the methods and variety described herein includes bluegrass cultivar 'Barvette' progeny bluegrass plants comprising a combination of at least two cultivar 'Barvette' traits or the cultivar 'Barvette' combination of traits listed in the Summary of the Invention, so that said progeny bluegrass plant is not significantly different for said traits than bluegrass variety 'Barvette' as determined at the 5% significance level when grown in the same environmental conditions. Using techniques described herein, molecular markers may be used to identify said progeny plant as a bluegrass variety 'Barvette' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of bluegrass variety 'Barvette' may also be characterized through their filial relationship with bluegrass variety 'Barvette', as for example, being within a certain number of breeding crosses of bluegrass variety 'Barvette'. A breeding cross is a cross made to introduce new genetics into the progeny, and is distinguished from a cross, such as a self or a sib cross, made to select among existing genetic alleles. The lower the number of breeding crosses in the pedigree, the closer the relationship between bluegrass variety 'Barvette' and its progeny. For example, progeny produced by the methods described herein may be within 1, 2, 3, 4 or 5 breeding crosses of bluegrass variety 'Barvette'.

Recurrent selection is a method used in a plant breeding program to improve a population of plants. 'Barvette' is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties. The number of parental plant varieties, populations, wild accessions, ecotypes, etc., that are used to generate a synthetic can vary from as little as 10 to as much as 500. Typically, about 100 to 300 varieties, populations, etc., are used a parents for the synthetic variety. Seed from the parental seed production plot of a synthetic variety can be sold to the farmer. Alternatively, seed from the parental seed production plot can subsequently undergo one or two generations of multiplication, depending on the amount of seed produced in the parental plot and the demand for seed.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation breeding is another method of introducing new traits into bluegrass variety 'Barvette'. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (such as from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, 1993. *Principles of Cultivar Development*, Macmillan Publishing Company. In addition, mutations created in other bluegrass plants may be used to produce a backcross conversion of bluegrass variety 'Barvette' that comprises such mutation.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing bluegrass variety 'Barvette'.

Isozyme Electrophoresis and RFLPs have been widely used to determine genetic composition. Shoemaker and Olsen, (O'Brien, S. J., (ed.) 1993. *Genetic Maps: Locus Maps of Complex Genomes*. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994. "RFLP Map of Soybean" p 299-309 In R. L. Phillips and I. K. Vasil (ed.) *DNA-Based Markers in Plants*. Kluwer Academic Press Dordrecht, the Netherlands. In switchgrass, Missaoui also described RFLP markers (Missaoui et al., 2006, "Molecular markers for the classification of switchgrass (*Panicum virgatum* L.) germplasm and to assess genetic diversity in three synthetic switchgrass populations" *Genetic Resources and Crop Evolution* 53:1291-1302).

SSR technology is currently the most efficient and practical marker technology; more marker loci can be routinely used and more alleles per marker locus can be found using SSRs in comparison to RFLPs. For example Diwan and Cregan, described a highly polymorphic microsatellite loci in soybean with as many as 26 alleles. (Diwan, N., and P. B. Cregan. 1997 "Automated sizing of fluorescent-labeled simple sequence repeat (SSR) markers to assay genetic variation in soybean". *Theor. Appl. Genet.* 95:220-225). Single Nucleotide Polymorphisms (SNPs) may also be used to identify the unique genetic composition of 'Barvette' and progeny varieties retaining that unique genetic composition. Various molecular marker techniques may be used in combination to enhance overall resolution.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Gene Conversions

When the term "bluegrass plant" is used in the context of the methods and varieties described herein, this also includes any gene conversions of that variety. The term gene converted plant as used herein refers to those bluegrass plants which are developed by a plant breeding technique called backcrossing wherein essentially all of the desired morphological and physiological characteristics of a variety are recovered in addition to the one or more genes transferred into the variety via the backcrossing technique. Backcrossing methods can be used with the methods and variety described herein to improve or introduce one or more characteristics into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental bluegrass plant that contributes the gene(s) for the desired characteristic is termed the nonrecurrent or donor parent. This terminology refers to the fact that the nonrecurrent parent is used one time in the backcross protocol and therefore does not recur. The parental bluegrass plant to which the gene or genes from the nonrecurrent parent are transferred is known as the recurrent parent as it is used for several rounds in the backcrossing protocol (Poehlman & Sleper, 1994; Fehr, *Principles of Cultivar Development* pp. 261-286 (1987)). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a bluegrass plant is obtained wherein essentially all of the desired morphological and physiological characteristics of the recurrent parent are recovered in the converted plant, in addition to the transferred gene(s) from the nonrecurrent parent.

The selection of a suitable recurrent parent is an important step for a successful backcrossing procedure. The goal of a backcross protocol is to alter or substitute one or more traits or characteristics in the original variety. To accomplish this, one or more genes of the recurrent variety is/are modified or substituted with the desired gene(s) from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic(s) or trait(s) being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic(s) has been successfully transferred.

Many traits have been identified that are not regularly selected for in the development of a new variety but that can be improved by backcrossing techniques. Traits may or may not be transgenic; examples of these traits include but are not limited to, male sterility, herbicide resistance, resistance for bacterial, fungal, or viral disease, insect resistance, male fertility, enhanced nutritional quality, industrial usage, yield stability and yield enhancement. These genes are generally inherited through the nucleus. Several of these traits are described in U.S. Pat. Nos. 5,959,185; 5,973,234 and 5,977,445; the disclosures of which are specifically hereby incorporated by reference for this purpose.

Introduction of a New Trait or Locus into 'Barvette'

Variety 'Barvette' represents a new base genetic variety into which a new locus or trait may be introgressed. Direct transformation and backcrossing represent two important methods that can be used to accomplish such an introgression. The term backcross conversion and locus conversion are used interchangeably to designate the product of a backcrossing program.

Backcross Conversions of 'Barvette'

A backcross conversion of 'Barvette' occurs when DNA sequences are introduced through backcrossing (Poehlman, *Breeding Field Crops*, p. 204 (1987), with 'Barvette' utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., "Marker-assisted Selection in Backcross Breeding" In: *Proceedings Symposium of the Analysis of Molecular Data*, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes vs unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in *Corn and Corn Improvement*, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, altered carbohydrate profile, industrial enhancements, disease resistance (bacterial, fungal or viral), insect resistance and herbicide resistance. In addition, an introgression site itself, such as an FRT site, Lox site or other site-specific integration site, may be inserted by backcrossing and utilized for direct insertion of one or more genes of interest into a specific plant variety. In some embodiments, the number of loci that may be backcrossed into 'Barvette' is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site-specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, *Breeding Field Crops*, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant and easily recognized traits.

One process for adding or modifying a trait or locus in bluegrass variety 'Barvette' comprises crossing 'Barvette' plants grown from 'Barvette' seed with plants of another bluegrass variety that comprise the desired trait or locus, selecting $F_1$ progeny plants that comprise the desired trait or locus to produce selected $F_1$ progeny plants, crossing the selected progeny plants with the 'Barvette' plants to produce backcross progeny plants, selecting for backcross progeny plants that have the desired trait or locus and the morphological characteristics of bluegrass variety 'Barvette' to produce selected backcross progeny plants; and backcrossing to 'Barvette' three or more times in succession to produce selected fourth or higher backcross progeny plants that comprise said trait or locus. The modified 'Barvette' may be further characterized as having the physiological and morphological characteristics of bluegrass variety 'Barvette' and/or may be characterized by percent similarity or identity to 'Barvette' as determined by SSR markers. The above method may be utilized with fewer backcrosses in appropriate situations, such as when the donor parent is highly related or markers are used in the selection step. Desired traits that may be used include those nucleic acids known in the art, some of which are mentioned herein, that will affect traits through nucleic acid expression or inhibition. Desired loci include the introgression of FRT, Lox and other sites for site specific integration, which may also affect a desired trait if a functional nucleic acid is inserted at the integration site.

Pedigree Breeding

Pedigree breeding starts with the crossing of two genotypes, such as 'Barvette' and another bluegrass variety having one or more desirable characteristics that is lacking or which complements 'Barvette'. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. In some embodiments, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a bluegrass variety may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the non-recurrent parent. This approach leverages the value and strengths of the recurrent parent for use in new bluegrass varieties.

Therefore, an embodiment is a method of making a backcross conversion of bluegrass variety 'Barvette', comprising the steps of crossing a plant of bluegrass variety 'Barvette' with a donor plant comprising a desired trait, selecting an $F_1$ progeny plant comprising the desired trait, and backcrossing the selected $F_1$ progeny plant to a plant of bluegrass variety 'Barvette'. This method may further comprise the step of obtaining a molecular marker profile of bluegrass variety 'Barvette' and using the molecular marker profile to select for a progeny plant with the desired trait and the molecular marker profile of 'Barvette'. In one embodiment the desired trait is a mutant gene or transgene present in the donor parent.

In addition, the above process and other similar processes described herein may be used to produce first generation progeny bluegrass seed by adding a step at the end of the process that comprises crossing 'Barvette' with the introgressed trait or locus with a different bluegrass plant and harvesting the resultant first generation progeny bluegrass seed.

Transgenic Bluegrass

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are inserted into the genome using transformation, are referred to herein collectively as "transgenes". In some embodiments of the invention, transgenic variants of the Kentucky bluegrass variety of the present invention may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transgenic variants of the claimed Kentucky bluegrass variety of the present invention.

One embodiment of the invention is a process for producing Kentucky bluegrass varieties further comprising a desired trait, said process comprising transforming a Kentucky bluegrass plant with a transgene that confers a desired trait. Another embodiment is the product produced by this process. In one embodiment the desired trait may be one or more of herbicide resistance, insect resistance, or disease resistance. The specific gene may be any known in the art or listed herein, including: a polynucleotide conferring resistance to imidazolinone, sulfonylurea, glyphosate, glufosinate, triazine, benzonitrile, cyclohexanedione, phenoxy proprionic acid and L-phosphinothricin; a polynucleotide encoding a *Bacillus thuringiensis* polypeptide, or a polynucleotide conferring resistance to one or more nematodes, *Phytophthora* root rot, or other fungi, or one or more viruses.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

A genetic trait which has been engineered into the genome of a particular Kentucky bluegrass plant may then be moved into the genome of another bluegrass variety using traditional breeding techniques that are well known in the plant breeding arts. For example, a backcrossing approach is commonly used to move a transgene from a transformed bluegrass variety into an already developed bluegrass variety, and the resulting backcross conversion plant would then comprise the transgene(s).

Various genetic elements can be introduced into the plant genome using transformation. These elements include, but are not limited to genes, coding sequences, inducible, constitutive, and tissue specific promoters, enhancing sequences, and signal and targeting sequences. For example, see the traits, genes and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed Kentucky bluegrass plants using transformation methods as described below to incorporate transgenes into the genetic material of the Kentucky bluegrass plant(s).

Expression Vectors for Kentucky Bluegrass Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. USA, 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986)). Other selectable marker genes confer resistance to herbicides such as glyphosate, glufosinate or bromoxynil (Comai et al., Nature 317:741-744 (1985), Gordon-Kamm et al., Plant Cell 2:603-618 (1990) and Stalker et al., Science 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., Science 233:478 (1986), Charest et al., Plant Cell Rep. 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., Plant Mol. Biol. Rep. 5:387 (1987), Teeri et al., EMBO J. 8:343 (1989), Koncz et al., Proc. Natl. Acad. Sci. USA 84:131 (1987), DeBlock et al., EMBO J. 3:1681 (1984)).

In vivo methods for visualizing GUS activity that do not require destruction of plant tissue are available (Molecular Probes publication 2908, IMAGENE GREEN, p. 1-4 (1993) and Naleway et al., J. Cell Biol. 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., Science 263: 802 (1994)). GFP and mutants of GFP may be used as screenable markers.

Expression Vectors for Kentucky Bluegrass Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, flowers, anthers, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is induced or activated in the presence of the correct stimulus. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression. Optionally, the inducible promoter is operably linked to a nucleotide sequence encoding a signal sequence which is operably linked to a gene for expression in perennial bluegrass. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., Proc. Natl. Acad. Sci. USA 90:4567-4571 (1993)); In2 gene from maize which responds to benzenesulfonamide herbicide safeners (Hershey et al., Mol. Gen. Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. USA 88:0421 (1991)).

B. Constitutive Promoters—A constitutive promoter is operably linked to a gene for expression in perennial bluegrass or the constitutive promoter is operably linked to a nucleotide sequence encoding a signal sequence which is operably linked to a gene for expression in bluegrass.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO 96/30530.

C. Tissue-specific or Tissue-preferred Promoters—A tissue-specific promoter is operably linked to a gene for expression in bluegrass. Optionally, the tissue-specific promoter is operably linked to a nucleotide sequence encoding a signal sequence which is operably linked to a gene for expression in bluegrass. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

Wang et al. discuss "Large Scale Identification, Mapping and Genotyping of Single-Nucleotide Polymorphisms in the Human Genome", *Science,* 280:1077-1082, 1998, and similar capabilities are becoming available for the bluegrass genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of interest. Through the transformation of bluegrass the expression of genes can be altered to enhance disease resistance, insect resistance, herbicide resistance and other traits. DNA sequences native to bluegrass as well as non-native DNA sequences can be transformed into bluegrass and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present invention, additional genes of interest can be expressed in transformed plants. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al. *Cell* 78:1089 (1994) (*Arabidopsis* RSP2 gene for resistance to *Pseudomonas syringae*), McDowell & Woffenden, (2003) *Trends Biotechnol.* 21(4): 178-83 and Toyoda et al., (2002) *Transgenic Res.* 11 (6):567-82.

B. A gene conferring resistance to a pest, such as a nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*); Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon,* 40 (11): 1515-1539; Ussuf et al. (2001) *Curr Sci.* 80 (7): 847-853; and Vasconcelos & Oliveira (2004) *Toxicon* 44 (4): 385-403. See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene, U.S. Pat. Nos. 7,145,060, 7,087,810 and 6,563,020.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 and U.S. Pat. No. 5,580,852, which disclose peptide derivatives of tachyplesin which inhibit fungal plant pathogens, and PCT application WO 95/18855 and U.S. Pat. No. 5,607,914 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., *Current Biology*, 5(2) (1995); Pieterse & Van Loon (2004) *Curr. Opin. Plant Bio.* 7(4):456-64 and Somssich (2003) *Cell* 113(7):815-6.

U. Antifungal genes. See Cornelissen and Melchers, *Plant Physiol.*, 101:709-712 (1993); Parijs et al., *Planta* 183:258-264 (1991) and Bushnell et al., *Can. J. of Plant Path.* 20(2): 137-149 (1998). Also see U.S. Pat. No. 6,875,907.

V. Detoxification genes, such as for fumonisin, beauvericin, moniliformin and zearalenone and their structurally related derivatives. For example, see U.S. Pat. No. 5,792,931.

W. Cystatin and cysteine proteinase inhibitors. See U.S. Pat. No. 7,205,453.

X. Defensin genes. See WO 03/000863 and U.S. Pat. No. 6,911,577.

Y. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids, aryloxyphenoxy propionate, and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627, 061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. No. 10/427, 692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. No. 5,892,009, U.S. Pat. No. 5,965,705, U.S. Pat. No. 5,929,305, U.S. Pat. No. 5,891,859, U.S. Pat. No. 6,417,428, U.S. Pat. No. 6,664,446, U.S. Pat. No. 6,706,866, U.S. Pat. No. 6,717,034, U.S. Pat. No. 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield. Also see WO 02/02776, WO 2003/052063, JP2002281975, U.S. Pat. No. 6,084,153, WO 01/64898, U.S. Pat. Nos. 6,177,275 and 6,107,547 (enhancement of nitrogen utilization and altered nitrogen responsiveness). For ethylene alteration, see US 20040128719, US 20030166197 and WO 2000/32761. For plant transcription factors or transcriptional regulators of abiotic stress, see e.g. US 20040098764 or US 20040078852.

Other genes and transcription factors that affect plant growth and agronomic traits such as yield, flowering, plant growth and/or plant structure, can be introduced or introgressed into plants, see e.g. WO 97/49811 (LHY), WO 98/56918 (ESD4), WO 97/10339 and U.S. Pat. No. 6,573,430 (TFL), U.S. Pat. No. 6,713,663 (FT), WO 96/14414 (CON), WO 96/38560, WO 01/21822 (VRN1), WO 00/44918 (VRN2), WO 99/49064 (GI), WO 00/46358 (FR1), WO 97/29123, U.S. Pat. No. 6,794,560, U.S. Pat. No. 6,307,126 (GAI), WO 99/09174 (D8 and Rht), and WO 2004/076638 and WO 2004/031349 (transcription factors).

Methods for Bluegrass Transformation

Numerous methods for plant transformation have been developed including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985); Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994)).

Following transformation of bluegrass target tissues, expression of the above-described selectable marker genes allows for preferential selection of transformed cells, tissues and/or plants, using regeneration and selection methods well known in the art.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" *Crop Science* 39:1464-1490 (1999), and Berry et al., Assessing Probability of Ancestry Using Simple Sequence Repeat Profiles: Applications to Maize Inbred Lines and Soybean Varieties" *Genetics* 165:331-342 (2003).

Particular markers used for these purposes are not limited to any particular set of markers, but are envisioned to include any type of marker and marker profile which provides a means of distinguishing varieties.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Tissue Culture

Further reproduction of the Kentucky bluegrass varieties of the present invention can occur by tissue culture and regeneration. Tissue culture of various tissues of Kentucky bluegrass and regeneration of plants therefrom is well known and widely published. For example, reference may be had to Bradley, D. E. et al. 2001. Effects of cultivar, explant treatment, and medium supplements on callus induction and plantlet regeneration in perennial bluegrass. *Int. Turfgrass Soc. Res. J.* 9:152-156; Cao, M. X., et al. 2006. Transformation of recalcitrant turfgrass cultivars through improvement of tissue culture and selection regime. *Plant, Cell, Tissue Organ Culture.* 85:307-316; WenZhen, L. et al. Factors effecting on tissue culture of perennial bluegrass (*Lolium perenne* L.). *Forest Res.* 2004, 17:95-101. Thus, another aspect of this invention is to provide cells which upon growth and differentiation produce Kentucky bluegrass plants having the physiological and morphological characteristics of the Kentucky bluegrass plants of the present invention.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, culms, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Tables

The following tables are provided to further illustrate the present invention and are not intended to limit the invention beyond the limitations set forth in the appended claims. The following tables characterize the outstanding traits and characteristics of Kentucky bluegrass variety 'Barvette' compared to the closest bluegrass varieties and standards.

Table 2 shows the morphological characteristics of Kentucky bluegrass variety 'Barvette' (also known by experimental name BAR VV 0709) compared to a number of other bluegrass varieties grown near Albany, Oreg. in 2006 and 2007. The Albany test was grown on Cloquato silt loam with a pH of 5.6-6.5 in the upper 21 inches. The trial consisted of a total of 75 plants per entry and there were three replications per entry with 25 plants per replication. The trial was conducted using completely random designs. The nursery was established in fall of 2005. Each entry was planted in 25 plant blocks in a 5×5 arrangement. The plant spacing within blocks and in-between the blocks was 2 feet. The nursery received:

1) 200 lbs/ac of 18-18-18 fertilizer in fall; 2) 200 lbs/ac of 33-0-12 in early spring; and 150 lbs/ac 46-0-0 in late spring. Fungicides were sprayed as needed to control any fungal diseases. Column 1 shows the cultivar name, columns 2 and 3 show the Julian heading dates for 2006 and 2007, respectively, column 4 shows the average Julian heading day, columns 5 and 6 show the plant height (cm) for 2006 and 2007, respectively, column 7 shows the average plant height (cm), columns 8 and 9 show the panicle length (cm) for 2006 and 2007, respectively, column 10 shows the average panicle length (cm), columns 11 and 12 show the flag leaf height (cm) for 2006 and 2007, respectively, column 13 shows the average flag leaf height (cm), columns 14 and 15 show the flag leaf length (cm) for 2006 and 2007, respectively, column 16 shows the average flag leaf length (cm), columns 17 and 18 show the flag leaf width (mm) for 2006 and 2007, respectively, column 19 shows the average flag leaf width (mm). To determine the LSD statistical differences among entries, subtract one entry's mean from another entry's mean; statistical differences occur when this value is larger than the corresponding LSD value. The coefficient of variation ($CV^2$) indicates the percent variation of the mean in each column.

Patch, which is caused by the fungus *Magnaporthe poae*. In the 2005 National Turfgrass Evaluation Program (NTEP) trials, 'Barvette' was top for Summer Patch resistance in three different trials. Table 3 shows the 2008 percent ratings of Summer Patch infection for selected Kentucky bluegrass cultivars, including 'Barvette', in the 2005 NTEP in Knoxville, Tenn. The trial consisted of a total of 110 entries. Column 1 shows the entry, columns 2-4 show the percent ratings of Summer Patch infection taken in July, August and September, respectively, and column 5 shows the mean percent. The Summer Patch data estimates the percent of given area with grass having Summer Patch infection, with a score of 0 indicating no infection, a score of 1 indicates 1-10% of area with Summer Patch infection, a score of 2 indicates 11-19% infection, a score of 3 indicates 20-39% infection, a score of 4 indicates 40-49% infection, a score of 5 indicates 50-59% infection, a score of 6 indicates 60-69% infection, a score of 7 indicates 70-79% infection, a score of 8 indicates 80-89% infection, and a score of 9 indicates greater than 90% of area infected with Summer Patch.

TABLE 2

Morphological characteristics

| | Heading date (Julian) | | | Plant height (cm) | | | Panicle length (cm) | | | Flag Leaf height (cm) | | | Flag Leaf length (cm) | | | Flag Leaf width (mm) | | |
|---|---|---|---|---|---|---|---|---|---|---|---|---|---|---|---|---|---|---|
| | 2006 | 2007 | AVG | 2006 | 2007 | AVG | 2006 | 2007 | AVG | 2006 | 2007 | AVG | 2006 | 2007 | AVG | 2006 | 2007 | AVG |
| 'Barvette' | 123 | 111 | 117 | 71.3 | 76 | 73.65 | 11.3 | 11.2 | 11.25 | 36.6 | 43.1 | 39.85 | 5.3 | 5.8 | 5.55 | 4.3 | 3.5 | 3.9 |
| Kenblue | 116 | 103 | 109 | 66.9 | 70.1 | 68.5 | 10.8 | 10.4 | 10.6 | 35.0 | 38.2 | 36.6 | 6.0 | 5.9 | 6.0 | 3.8 | 2.2 | 3.0 |
| Lato | 126 | 112 | 119 | 76.4 | 79.2 | 77.8 | 14.9 | 16.0 | 15.5 | 38.8 | 45.3 | 42.1 | 10.8 | 10.8 | 10.8 | 6.7 | 4.5 | 5.6 |
| Slezenska | 128 | 120 | 124 | 69.3 | 78.9 | 74.1 | 12.6 | 14.1 | 13.4 | 41.2 | 44.8 | 43.0 | 6.9 | 9.2 | 8.1 | 5.0 | 4.3 | 4.7 |
| Baron | 128 | 112 | 120 | 42.9 | 53.3 | 48.1 | 7.8 | 8.3 | 8.1 | 21.1 | 26.8 | 24.0 | 3.9 | 5.0 | 4.5 | 3.7 | 3.6 | 3.7 |
| Barimpala | 123 | 113 | 118 | 65.2 | 71.4 | 68.3 | 10.9 | 10.9 | 10.9 | 32.0 | 37.7 | 34.9 | 6.4 | 5.5 | 6.0 | 4.5 | 3.2 | 3.9 |
| Bariris | 127 | 115 | 121 | 60.0 | 77.5 | 68.8 | 9.7 | 11.6 | 10.7 | 34.8 | 44.0 | 39.4 | 5.9 | 6.0 | 6.0 | 4.3 | 3.5 | 3.9 |
| Baronie | 128 | 113 | 121 | 61.6 | 65.4 | 63.5 | 8.9 | 10.6 | 9.8 | 33.9 | 35.9 | 34.9 | 4.8 | 6.0 | 5.4 | 3.5 | 3.7 | 3.6 |
| Midnight | 132 | 129 | 131 | 46.6 | 61.3 | 54.0 | 8.0 | 9.2 | 8.6 | 25.3 | 34.3 | 29.8 | 4.8 | 6.9 | 5.9 | 3.3 | 3.3 | 3.3 |
| Julia | 127 | 114 | 120 | 63.2 | 71.7 | 67.5 | 9.6 | 11.5 | 10.6 | 36.2 | 40.8 | 38.5 | 5.3 | 5.9 | 5.6 | 3.8 | 3.2 | 3.5 |
| Full Moon | 121 | 108 | 114 | 46.0 | 46.3 | 46.2 | 11.0 | 10.1 | 10.6 | 23.3 | 21.9 | 22.6 | 3.8 | 4.3 | 4.1 | 3.4 | 3.2 | 3.3 |
| Barzan | 125 | 111 | 118 | 47.0 | 53.7 | 50.4 | 6.9 | 7.6 | 7.3 | 23.5 | 27.5 | 25.5 | 3.6 | 3.2 | 3.4 | 3.5 | 2.6 | 3.1 |
| Baritone | 127 | 114 | 120 | 59.3 | 74.3 | 66.8 | 9.8 | 11.0 | 10.4 | 32.7 | 43.6 | 38.2 | 5.9 | 6.1 | 6.0 | 3.4 | 3.6 | 3.5 |
| Bristol | 128 | 115 | 121 | 58.8 | 66.4 | 62.6 | 9.2 | 11.2 | 10.2 | 28.8 | 34.1 | 31.5 | 4.6 | 5.6 | 5.1 | 3.6 | 3.7 | 3.7 |
| Shamrock | 125 | 109 | 117 | 52.7 | 61.6 | 57.2 | 9.0 | 8.9 | 9.0 | 27.3 | 31.4 | 29.4 | 4.8 | 3.7 | 4.3 | 4.2 | 3.0 | 3.6 |
| LSD (P = .05) | 2 | 4 | | 5.3 | 10.5 | | 1.5 | 1.4 | | 4.1 | 7.6 | | 0.9 | 1.1 | | 0.6 | 0.7 | |
| Standard Deviation | 1 | 3 | | 3.2 | 6.4 | | 0.9 | 0.9 | | 2.5 | 4.6 | | 0.5 | 0.7 | | 0.4 | 0.5 | |
| CV | 1 | 2 | | 5.6 | 9.5 | | 9.3 | 8.3 | | 8.2 | 12.7 | | 10.3 | 11.8 | | 8.5 | 13.2 | |

Kentucky bluegrass variety 'Barvette' (BAR VV 0709) was entered into the 2005 National Turfgrass Evaluation Program (NTEP) for Kentucky bluegrass varieties at various locations across the United States and was rated top for at least six traits, including resistance to Summer Patch, superior performance for traffic tolerance and recovery from intense traffic events, billbug (*Sphenophorus* spp.) grub resistance, reduced damage by white grubs (e.g. *Ataenius spretulus, Popilla japonica, Cyclocephala* spp., *Phyllophaga* spp.), high stem rust resistance caused by the fungus *Puccinia graminis*, and excellent tolerances to summer stresses. Tables 3-16 show data from trials of bluegrass varieties that were established in 2005 for the NTEP. Most trials consisted of greater than 100 entries and the data in Tables 3-16 show a selection of the best varieties for each trait and also include the 2005 NTEP bluegrass standards: Shamrock, Kenblue, Julia, Nu Density, Reveille, America, Baron and Midnight.

One of the outstanding characteristics of Kentucky bluegrass variety 'Barvette' is its resistance to the disease Summer

TABLE 3

Summer Patch damage (Knoxville, Tenessee)

Percent Summer Patch infection

| Entry | July | August | September | Mean |
|---|---|---|---|---|
| 'Barvette' (BAR VV 0709) | 0 | 2.7 | 2.7 | 1.8 |
| JUMP START (PST-109-752) | 3.3 | 1.7 | 2.7 | 2.6 |
| EVERGLADE | 0 | 2.7 | 5.3 | 2.7 |
| MYSTERE | 0 | 2.7 | 5.3 | 2.7 |
| WASHINGTON | 3.3 | 4 | 5 | 4.1 |
| ALEXA II (J-2404) | 5.3 | 2.7 | 5.3 | 4.4 |
| DIVA | 4 | 7.7 | 8 | 6.6 |
| MIDNIGHT | 7.3 | 7.7 | 8 | 7.7 |
| SKYE | 12.7 | 5 | 5.3 | 7.7 |
| JULIA | 7.7 | 6 | 10.3 | 8 |
| NU DESTINY | 8.7 | 10.7 | 8 | 9.1 |
| SOLAR ECLIPSE (J-2399) | 16.7 | 4 | 7.3 | 9.3 |
| REVEILLE | 6.7 | 9.7 | 12 | 9.4 |

TABLE 3-continued

Summer Patch damage (Knoxville, Tenessee)

| Entry | Percent Summer Patch infection | | | |
|---|---|---|---|---|
| | July | August | September | Mean |
| BARON | 14.3 | 6.7 | 8.3 | 9.8 |
| BANDERA (SPTR 2LM95) | 7.7 | 9.3 | 12.7 | 9.9 |
| AURA (A99-2559) | 10.7 | 9.3 | 10 | 10 |
| NUCHICAGO (J-1466) | 18.3 | 7.7 | 6 | 10.7 |
| AMERICA | 8 | 13.3 | 12 | 11.1 |
| WASHINGTON II (RAD-343) | 8.3 | 13.7 | 12 | 11.3 |
| AWARD | 17.3 | 9.3 | 7.7 | 11.4 |
| RUGBY II | 11 | 10 | 14 | 11.7 |
| KENBLUE | 12.3 | 12.3 | 12.7 | 12.4 |
| SOMBRERO (CP 76-9068) | 16 | 13.7 | 11 | 13.6 |
| EXCURSION | 20 | 13 | 11.7 | 14.9 |
| SHAMROCK | 11 | 16.7 | 21.7 | 16.4 |
| GREENTEAM (CPP 821) | 15.7 | 16.7 | 18.3 | 16.9 |
| PROSPERITY | 24 | 24 | 24.3 | 24.1 |
| EMBLEM (PST-Y2K-169) | 31.7 | 25 | 16.7 | 24.4 |
| Highest Rated Entry | 33.3 | 40 | 48.3 | 36.7 |
| Lowest Rated Entry | 0 | 0 | 2.7 | 1.8 |
| LSD VALUE | 17.5 | 12.1 | 15.2 | 10.5 |
| C.V. (%) | 75.2 | 63.2 | 68.4 | 53.6 |

As shown in Table 3, 'Barvette' was the top entry and exhibited the lowest mean incidence of Summer Patch when compared to the other entries.

Table 4 shows the 2010 data for mean percent Summer Patch ratings of selected Kentucky bluegrass cultivars, including 'Barvette', in the 2005 National Turfgrass Evaluation Program (NTEP) in Stillwater, Okla. The trial was established in 2005 and consisted of a total of 110 entries. Column 1 shows the entry and column 2 shows the mean rating for Summer Patch incidence. The Summer Patch data estimates the percent of given area with grass having Summer Patch infection, with a score of 0 indicating no infection, a score of 1 indicates 1-10% of area with Summer Patch infection, a score of 2 indicates 11-19% infection, a score of 3 indicates 20-39% infection, a score of 4 indicates 40-49% infection, a score of 5 indicates 50-59% infection, a score of 6 indicates 60-69% infection, a score of 7 indicates 70-79% infection, a score of 8 indicates 80-89% infection, and a score of 9 indicates greater than 90% of area infected with Summer Patch.

TABLE 4

Summer Patch damage (Stillwater, Oklahoma)

| Entry | Mean Rating |
|---|---|
| 'Barvette' (BAR VV 0709) | 1 |
| Midnight | 2.3 |
| Alexa II (J-2404) | 2.7 |
| Excursion | 2.7 |
| NuChicago (J-1466) | 3 |
| Award | 3.3 |
| Everglade | 3.3 |
| Solar Eclipse (J-2399) | 3.3 |
| Mystere | 3.7 |
| Nu Destiny | 3.7 |
| Kenblue | 4.3 |
| Reveille | 4.3 |
| Baron | 4.4 |
| Aura (A99-2559) | 4.7 |
| Bandera (SPTR 2LM95) | 4.7 |
| America | 5 |
| Jump Start (PST-109-752) | 5 |
| Rugby II | 5 |
| Sombrero (CP 76-9068) | 5 |
| Greenteam (CPP 821) | 5.3 |
| Prosperity | 5.3 |
| Skye | 5.3 |
| Washington | 5.3 |

TABLE 4-continued

Summer Patch damage (Stillwater, Oklahoma)

| Entry | Mean Rating |
|---|---|
| Diva | 5.7 |
| Shamrock | 5.7 |
| Emblem (PST-Y2K-169) | 6 |
| Julia | 6 |
| Highest Rated Entry | 1 |
| Lowest Rated Entry | 6.7 |
| LSD (P = .10) | 1.64 |
| Standard Deviation | 1.22 |
| CV | 29.91 |

As shown in Table 4, 'Barvette' was the highest rated entry and exhibited the lowest incidence of Summer Patch when compared to the other entries.

Table 5 shows the mean percent Summer Patch ratings of selected Kentucky bluegrass cultivars, including 'Barvette', in the 2005 National Turfgrass Evaluation Program (NTEP) grown at Raleigh, N.C. The 2005 NTEP Kentucky bluegrass trial had 114 Kentucky bluegrass entries and was planted on Oct. 18, 2005 at the NC State University Turfgrass Research Facility. Summer Patch (*Magnaporthe poae*) readings were collected on 2 separate rating dates of Jul. 14, 2010 and Sep. 27, 2010. Fall density and percent living ground cover data were also collected. Analysis of variance utilizing the Statistical Analysis System (General Linear Model (GLM) procedure) was conducted on these data sets. Mean separation tests were performed for block, date, and treatment (variety) at $\alpha=0.10$. Column 1 shows the entry and column 2 shows the mean rating for Summer Patch incidence. The Summer Patch data estimates the percent of given area with grass having Summer Patch infection, with a score of 0 indicating no infection, a score of 1 indicates 1-10% of area with Summer Patch infection, a score of 2 indicates 11-19% infection, a score of 3 indicates 20-39% infection, a score of 4 indicates 40-49% infection, a score of 5 indicates 50-59% infection, a score of 6 indicates 60-69% infection, a score of 7 indicates 70-79% infection, a score of 8 indicates 80-89% infection, and a score of 9 indicates greater than 90% of area infested with Summer Patch.

TABLE 5

Summer Patch damage (Raleigh, North Carolina)

| Entry | Mean |
|---|---|
| 'Barvette' (BAR VV 0709) | 0 |
| NuChicago (J-1466) | 1.17 |
| Mystere | 1.67 |
| Reveille | 1.83 |
| Skye | 1.83 |
| Midnight | 2 |
| Solar Eclipse (J-2399) | 2.17 |
| Alex II (J-2404) | 2.33 |
| Award | 2.33 |
| Bandera (SPTR 2LX95) | 2.33 |
| Excursion | 2.33 |
| America | 2.67 |
| Diva | 2.67 |
| Kenblue | 2.67 |
| Washington | 2.67 |
| Aura (A99-2559) | 2.83 |
| Prosperity | 2.83 |
| Nu Destiny | 3 |
| Greenteam (CPP 821) | 3.17 |
| Rugby II | 3.17 |
| Thermal Blue | 3.5 |
| Washington II (RAD-343) | 3.67 |
| Everglade | 3.83 |
| Shamrock | 4 |
| Baron | 4.5 |

TABLE 5-continued

Summer Patch damage (Raleigh, North Carolina)

| Entry | Mean |
|---|---|
| Julia | 5.17 |
| Emblem (PST-Y2K-169) | 5.67 |
| Sombrero (CP 76-9068) | 5.83 |
| Highest Ranking Value | 0 |
| Lowest Ranking Value | 6.5 |
| LSD (0.05) | 1 |
| Error Mean Square | 0.83 |

As shown in Table 5, 'Barvette' was the only variety to exhibit no Summer Patch infection when compared to the other entries. 'Barvette' is the first known bluegrass that can withstand or recover very quickly from Summer Patch. The data in Tables 3-5 show that 'Barvette' was the top entry for Summer Patch resistance in three different trials. There were no other varieties that made the top six varieties in all three trials; only three varieties made the top six in two of the three trials, Midnight, Alexa II, and Mystere.

In addition to having resistance to Summer Patch, Kentucky bluegrass variety 'Barvette' also exhibits exceptional traffic tolerance and recovers very quickly from traffic damage, which makes 'Barvette' particularly suitable for use in lawns, athletic fields, golf courses, sod, sod farms, parks, recreation areas, and other locations where excellent turf quality is desired. Current commercial Kentucky bluegrass varieties do not fully recover from intense traffic.

Table 6 shows the recovery of 'Barvette' compared to other Kentucky bluegrass cultivars and selections that were subjected to traffic (wear) in November 2008 in a turf trial seeded in September 2005 at North Brunswick, N.J. The trial included all entries of the 2005 National Turfgrass Evaluation Program (NTEP) Kentucky bluegrass Test. Column 1 shows the entry, column 2 shows the percent cover 148 days after wear (DAW), column 3 shows the percent cover 171 DAW, column 4 shows the percent cover 184 DAW, column 5 shows the percent cover 202 DAW, column 6 shows the percent cover 237 DAW, and column 7 shows the traffic tolerance rated after 36 passes of a wear stimulator. The turfgrass recovery is shown in terms of percent living ground cover using a 0-100% scale, where 0 indicates the absence of turfgrass canopy and 100 indicates a full canopy.

TABLE 6

Traffic recovery

| Entry | 148 DAW 2-Apr-09 | 171 DAW 24-Apr-09 | 184 DAW 8-May-09 | 202 DAW 26-May-09 | 237 DAW 30-Jun-09 | Traffic tolerance |
|---|---|---|---|---|---|---|
| 'Barvette' (BAR VV 0709) | 35 | 55 | 90 | 95 | 100 | 53.3 |
| Mystere | 18.3 | 26.7 | 51.7 | 65 | 86.7 | 10 |
| Greenteam | 16.7 | 23.3 | 45 | 75 | 91.7 | 68.3 |
| Jump Start | 8.3 | 18.3 | 43.3 | 61.7 | 85 | 15 |
| Kenblue | 15 | 23.2 | 41.7 | 66.7 | 81.7 | 6.7 |
| Skye | 11.7 | 21.7 | 41.7 | 71.7 | 88.3 | 25 |
| Sombrero | 13.3 | 18.3 | 41.7 | 83.3 | 98.3 | 73.3 |
| Julia | 13.3 | 16.7 | 38.3 | 66.7 | 83.3 | 51.7 |
| Aura | 16.7 | 18.3 | 35 | 56.7 | 78.3 | 25 |
| Washington | 16.7 | 17.7 | 35 | 68.3 | 75 | 36.7 |
| Reveille | 13.3 | 16.7 | 31.7 | 61.7 | 86.7 | 23.3 |
| Baron | 10 | 13.3 | 30 | 50 | 90 | 26.7 |
| Washington II (RAD 343) | 15 | 11.7 | 26.7 | 53.3 | 85 | 25 |
| Diva | 8.3 | 11.7 | 25 | 41.7 | 81.7 | 20 |
| Excursion | 8.3 | 16.7 | 23.3 | 53.3 | 86.7 | 48.3 |
| Shamrock | 8.3 | 16.7 | 23.3 | 46.7 | 86.7 | 25 |
| Emblem | 8.3 | 11.7 | 21.7 | 50 | 96.7 | 71.7 |
| Everglade | 5 | 10 | 21.7 | 51.7 | 85 | 43.3 |
| Nu Destiny | 5 | 11.7 | 20 | 50 | 86.7 | 48.3 |
| NuChicago | 5 | 6.7 | 18.3 | 46.7 | 80 | 38.3 |
| Rugby II | 6.7 | 8.3 | 16.7 | 46.7 | 83.3 | 41.7 |
| Alexa II | 5 | 10 | 15 | 41.7 | 80 | 43.3 |
| Bandera | 5 | 8.3 | 13.3 | 30 | 78.3 | 10 |
| Midnight | 5 | 6.7 | 13.3 | 31.7 | 81.7 | 50 |
| Prosperity | 5 | 6.7 | 13.3 | 30 | 73.3 | 51.7 |
| Solar Eclipse | 5 | 6.7 | 13.3 | 41.7 | 83.3 | 48.3 |
| America | 6.7 | 6.7 | 11.7 | 26.7 | 71.7 | 11.7 |
| Award | 5 | 10 | 11.7 | 31.7 | 81.7 | 43.3 |
| Highest Rated Entry | 35 | 55 | 90 | 95 | 100 | 68.3 |
| Lowest Rated Entry | 5 | 6.7 | 10 | 16.7 | 50 | 8.3 |
| LSD (α = 0.05) | 6.1 | 9 | 14 | 19.4 | 15.8 | 16.1 |

As shown in Table 6, 'Barvette' exhibited the greatest recovery from traffic when compared to the other entries at all time points and displayed 100% recovery by 237 days after wear (DAW).

Table 7 shows the traffic tolerance and traffic recovery of 'Barvette' compared to other Kentucky bluegrass cultivars and selections that were subjected to traffic (wear) in July 2009 in a turf trial seeded in September 2005 at North Brunswick, N.J. The trial included 114 entries of the 2005 National Turfgrass Evaluation Program (NTEP) Kentucky bluegrass Test. Column 1 shows the entry, column 2 shows the percent living cover with no traffic on Jul. 22, 2009, column 3 shows the traffic tolerance in terms of percent cover after 36 passes of a traffic simulator, column 4 shows the recovery of turfgrass as percent cover 7 days after wear (DAW), column 5 shows the turfgrass recovery 33 DAW, and column 6 shows the turfgrass recovery 98 DAW. The turfgrass recovery is shown in terms of percent living ground cover using a 0-100% scale, where 0 indicates the absence of turfgrass canopy and 100 indicates a full canopy.

TABLE 7

Traffic tolerance and recovery

| Entry | No traffic 22-Jul-09 | Traffic tolerance 24-Jul-09 | Traffic recovery | | |
|---|---|---|---|---|---|
| | | | 7 DAW 3-Aug-09 | 33 DAW 26-Aug-09 | 98 DAW 30-Oct-09 |
| 'Barvette' (BAR VV 0709) | 98.3 | 58.3 | 58.3 | 78.3 | 96.7 |
| Emblem | 96.7 | 75 | 71.7 | 61.7 | 86.7 |
| Excursion | 85 | 61.7 | 61.7 | 61.7 | 88.3 |
| Everglade | 83.3 | 56.7 | 60 | 50 | 78.3 |
| Nu Destiny | 83.3 | 58.3 | 56.7 | 48.3 | 80 |
| Greenteam | 91.7 | 80 | 75 | 43.3 | 63.3 |
| Mystere | 76.7 | 23.3 | 28.3 | 43.3 | 73.3 |
| NuChicago | 81.7 | 51.7 | 50 | 43.3 | 76.7 |
| Rugby II | 76.7 | 41.7 | 45 | 43.3 | 73.3 |
| Midnight | 81.7 | 60 | 56.7 | 41.7 | 81.7 |
| Reveille | 78.3 | 41.7 | 43.3 | 41.7 | 73.3 |
| Skye | 90 | 53.3 | 50 | 41.7 | 75 |
| Sombrero | 100 | 86.7 | 75 | 41.7 | 58.3 |
| Alexa II | 78.3 | 51.7 | 51.7 | 40 | 76.7 |
| Award | 80 | 53.3 | 53.3 | 40 | 80 |
| Julia | 83.3 | 68.3 | 63.3 | 40 | 58.3 |
| Jump Start | 83.3 | 51.7 | 51.7 | 40 | 61.7 |
| Solar Eclipse | 78.3 | 55 | 55 | 40 | 70 |
| Shamrock | 80 | 41.7 | 43.3 | 35 | 65 |
| Aura | 81.7 | 40 | 38.3 | 33.3 | 60 |
| Kenblue | 73.3 | 20 | 23.3 | 33.3 | 70 |
| Baron | 83.3 | 43.3 | 46.7 | 30 | 66.7 |
| Prosperity | 76.7 | 58.3 | 55 | 30 | 55 |
| Washington | 81.7 | 46.7 | 40 | 28.3 | 60 |
| Bandera | 75 | 30 | 26.7 | 26.7 | 60 |
| Washington II (RAD 343) | 83.3 | 46.7 | 41.7 | 26.7 | 53.3 |
| America | 70 | 16.7 | 20 | 21.7 | 53.3 |
| Diva | 81.7 | 25 | 30 | 21.7 | 58.3 |
| Highest Rated Entry | 100 | 86.7 | 75 | 78.3 | 96.7 |
| Lowest Rated Entry | 56.7 | 10 | 13.3 | 18.3 | 50 |
| LSD (α = 0.05) | 12.4 | 18.6 | 16.7 | 18.5 | 18.5 |

As shown in Table 7, 'Barvette' exhibits exceptional recovery from traffic and by 98 days after wear was almost completely recovered, with 96.7% living cover.

Table 8 shows the 2010 traffic recovery data for percent living ground cover and compaction ratings of 'Barvette' compared to other Kentucky bluegrass cultivars and selections grown under traffic stress at North Brunswick, N.J. in the 2005 National Turfgrass Evaluation Program (NTEP). The trial was established in 2005 and included 114 entries. Column 1 shows the entry, column 2 shows the percent living ground cover before traffic, column 3 shows the percent living ground cover after 36 passes of a traffic simulator, column 4 shows the percent cover 8 days after wear (DAW), column 5 shows the compaction in terms of percent living ground cover 22 DAW, and column 6 shows the recovery in terms of percent cover 49 DAW. The turfgrass recovery is shown in terms of percent living ground cover using a 0-100% scale, where 0 indicates the absence of turfgrass canopy and 100 indicates a full canopy.

TABLE 8

Traffic compaction and recovery

| Entry | Before traffic 4-May | 36 passes of traffic simulator 6-May | After traffic 8 DAW 14-May | Compaction 22 DAW 28-May | Traffic recovery 49 DAW 24-Jun |
|---|---|---|---|---|---|
| 'Barvette' (BAR VV 0709) | 97.7 | 66.7 | 56.7 | 85 | 95 |
| GREENTEAM (CPP 821) | 86.3 | 71.7 | 66.7 | 78.3 | 83.3 |

TABLE 8-continued

Traffic compaction and recovery

| Entry | Before traffic 4-May | 36 passes of traffic simulator 6-May | After traffic 8 DAW 14-May | Compaction 22 DAW 28-May | Traffic recovery 49 DAW 24-Jun |
|---|---|---|---|---|---|
| JULIA | 86.3 | 53.3 | 56.7 | 68.3 | 80 |
| SOMBRERO (CP 76-9068) | 73.3 | 61.7 | 53.3 | 65 | 83.3 |
| AURA (A99-2559) | 88 | 20 | 35 | 51.7 | 68.3 |
| EMBLEM (PST-Y2K-169) | 78 | 51.7 | 43.3 | 51.7 | 73.3 |
| JUMP START (PST-109-752) | 83.3 | 43.3 | 41.7 | 51.7 | 76.7 |
| KENBLUE | 86.7 | 31.7 | 36.7 | 51.7 | 66.7 |
| RUGBY II | 83 | 38.3 | 38.3 | 51.7 | 68.3 |
| EXCURSION | 91.3 | 38.3 | 43.3 | 50 | 76.7 |
| BARON | 79.7 | 31.7 | 31.7 | 48.3 | 70 |
| MYSTERE | 93 | 33.3 | 36.7 | 48.3 | 71.7 |
| NU DESTINY | 88 | 38.3 | 48.3 | 48.3 | 66.7 |
| WASHINGTON | 88 | 31.7 | 38.3 | 48.3 | 73.3 |
| SHAMROCK | 80 | 33.3 | 35 | 45 | 61.7 |
| BANDERA (SPTR 2LM95) | 76.7 | 28.3 | 28.3 | 43.3 | 63.3 |
| REVEILLE | 81.3 | 30 | 36.7 | 41.7 | 68.3 |
| SKYE | 81.7 | 23.3 | 33.3 | 41.7 | 73.3 |
| EVERGLADE | 89.7 | 41.7 | 45 | 40 | 68.3 |
| AWARD | 88 | 33.3 | 31.7 | 36.7 | 63.3 |
| PROSPERITY | 63.3 | 43.3 | 36.7 | 36.7 | 61.7 |
| WASHINGTON II (RAD-343) | 75 | 23.3 | 31.7 | 36.7 | 65 |
| NUCHICAGO (J-1466) | 75 | 25 | 31.7 | 35 | 56.7 |
| ALEXA II (J-2404) | 85 | 25 | 33.3 | 31.7 | 60 |
| SOLAR ECLIPSE (J-2399) | 60 | 20 | 23.3 | 30 | 51.7 |
| DIVA | 75 | 30 | 28.3 | 28.3 | 61.7 |
| AMERICA | 60 | 15 | 15 | 18.3 | 46.7 |
| Highest Rated Entry | 97.7 | 71.7 | 66.7 | 85 | 95 |
| Lowest Rated Entry | 48.3 | 13.3 | 13.3 | 13.3 | 35 |
| LSD VALUE | 32.9 | 21.5 | 25.2 | 26.7 | 21.7 |
| C.V. (%) | 17 | 35.8 | 34.4 | 32.7 | 17.1 |

As shown in Table 8, 'Barvette' exhibits exceptional recovery from traffic and by 22 and 49 days after wear has the highest percent living cover of all entries, with 85% and 95% living cover, respectively.

Table 9 shows the 2010 traffic recovery data in terms of percent living ground cover before and after traffic for 'Barvette' compared to other Kentucky bluegrass cultivars in the 2005 NTEP trials from turf grown in East Lansing, Mich. The trial was established in 2005 and included 114 entries. For this trial, the 2010 traffic was applied between Aug. 25, 2010 and Sep. 23, 2010. Column 1 shows the entry, column 2 shows the recovery from traffic applied in 2009 as of April 2010, column 3 shows the recovery from 2009 traffic in May 2010, column 4 shows the recovery from 2009 traffic in June 2010, column 5 shows the percent living cover before 2010 traffic on August 25, column 6 shows the recovery after traffic as of September 23 (0 days after wear (DAW)), column 7 shows the recovery after traffic as of October 21 (29 DAW), and column 8 shows the recovery after traffic as of November 18 (58 DAW). The turfgrass recovery is shown in terms of percent living ground cover using a 0-100% scale, where 0 indicates the absence of turfgrass canopy and 100 indicates a full canopy.

TABLE 9

Traffic recovery

| | Recovery from 2009 traffic | | | Before 2010 traffic | Recovery after 2010 traffic application | | |
|---|---|---|---|---|---|---|---|
| | | | | | 0 DAW | 29 DAW | 58 DAW |
| Entry | April | May | June | 25-Aug | 23-Sep | 21-Oct | 18-Nov |
| 'Barvette' (BAR VV 0709) | 90 | 88.3 | 94.3 | 97 | 90 | 65 | 70 |
| WASHINGTON | 65 | 83.3 | 86.7 | 95.7 | 90 | 53.3 | 60 |
| AWARD | 58.3 | 73.3 | 81.7 | 88.3 | 83.3 | 51.7 | 53.3 |
| WASHINGTON II (RAD-343) | 66.7 | 86.7 | 95 | 97 | 83.3 | 46.7 | 53.3 |
| AMERICA | 51.7 | 65 | 76.7 | 87.3 | 75 | 46.7 | 45 |
| KENBLUE | 65 | 73.3 | 76.7 | 86.7 | 66.7 | 45 | 41.7 |
| SKYE | 76.7 | 90 | 91 | 97 | 83.3 | 43.3 | 45 |

TABLE 9-continued

Traffic recovery

| | Recovery from 2009 traffic | | | Before 2010 traffic | Recovery after 2010 traffic application | | |
|---|---|---|---|---|---|---|---|
| Entry | April | May | June | 25-Aug | 23-Sep | 21-Oct | 18-Nov |
| | | | | | 0 DAW | 29 DAW | 58 DAW |
| BARON | 60 | 76.7 | 85 | 90 | 76.7 | 40 | 45 |
| RUGBY II | 63.3 | 78.3 | 85 | 93.3 | 65 | 40 | 51.7 |
| NU DESTINY | 60 | 75 | 83.3 | 88.3 | 73.3 | 38.3 | 41.7 |
| ALEXA II (J-2404) | 55 | 68.3 | 78.3 | 85 | 71.7 | 38.3 | 36.7 |
| NUCHICAGO (J-1466) | 50 | 68.3 | 75 | 85 | 73.3 | 35 | 36.7 |
| SOLAR ECLIPSE (J-2399) | 43.3 | 55 | 70 | 80 | 73.3 | 35 | 36.7 |
| PROSPERITY | 45 | 63.3 | 70 | 73.3 | 71.7 | 35 | 33.3 |
| BANDERA (SPTR 2LM95) | 48.3 | 58.3 | 73.3 | 76.7 | 68.3 | 35 | 38.3 |
| SOMBRERO (CP 76-9068) | 45 | 60 | 71.7 | 81.7 | 60 | 35 | 36.7 |
| EXCURSION | 45 | 58.3 | 76.7 | 85 | 76.7 | 33.3 | 35 |
| MYSTERE | 50 | 75 | 76.7 | 86.7 | 71.7 | 33.3 | 41.7 |
| JULIA | 35 | 51.7 | 70 | 83.3 | 66.7 | 31.7 | 33.3 |
| EVERGLADE | 38.3 | 55 | 71.7 | 75 | 61.7 | 31.7 | 35 |
| JUMP START (PST-109-752) | 41.7 | 60 | 65 | 70 | 56.7 | 30 | 31.7 |
| DIVA | 36.7 | 45 | 65 | 78.3 | 65 | 28.3 | 35 |
| REVEILLE | 43.3 | 51.7 | 70 | 80 | 63.3 | 28.3 | 35 |
| GREENTEAM (CPP 821) | 38.3 | 45 | 60 | 61.7 | 51.7 | 28.3 | 41.7 |
| SHAMROCK | 36.7 | 55 | 68.3 | 70 | 33.3 | 28.3 | 35 |
| MIDNIGHT | 36.7 | 46.7 | 66.7 | 70 | 58.3 | 25 | 30 |
| EMBLEM (PST-Y2K-169) | 39 | 47.3 | 50 | 60 | 46.7 | 23.3 | 28.3 |
| Highest Rated Entry | 90 | 90 | 94.3 | 97 | 90 | 65 | 70 |
| Lowest Rated Entry | 15.7 | 27.3 | 41.7 | 51.7 | 38.3 | 13.3 | 16.7 |
| LSD VALUE | 36.7 | 49.5 | 42.9 | 53.4 | 44 | 25.4 | 30.7 |
| C.V. (%) | 31.4 | 28.3 | 20.7 | 18.9 | 23.4 | 30.6 | 29.4 |

As shown in Table 9, 'Barvette' had the greatest recovery of all entries tested for all time points, with the exception of the May recovery from 2009. Although, varieties Midnight, Alexa II, and Mystere made the top six entries in two of the three Summer Patch trials, the same varieties were not close to 'Barvette' in the traffic trials for tolerance and recovery. Taken together, the data from Tables 3-9 show that 'Barvette' has the unique and surprising combination of resistance to Summer Patch and increased traffic tolerance and traffic recovery, which is not observed in any other known bluegrass variety.

Billbugs and white grubs can devastate Kentucky bluegrass; however, the 2005 NTEP trials acknowledged 'Barvette' for having the highest tolerance against these bluegrass pests. Table 10 shows the 2008 data for billbug damage of 'Barvette' compared to other Kentucky bluegrass cultivars and selections in the 2005 NTEP trials from turf grown in Logan, Utah. The trial was established in 2005 and consisted of a total of 110 entries. The billbug damage data estimates the percent of area with billbug damage using a 1 to 9 rating scale with a score of 0 indicating no damage, a score of 1 indicates 1-10% of area with billbug damage, a score of 2 indicates 11-19% of area with billbug damage, a score of 3 indicates 20-39% of area with billbug damage, a score of 4 indicates 40-49% of area with billbug damage, a score of 5 indicates 50-59% of area with billbug damage, a score of 6 indicates 60-69% of area with billbug damage, a score of 7 indicates 70-79% of area with billbug damage, a score of 8 indicates 80-89% of area with billbug damage, and a score of 9 indicates greater than 90% of area with billbug damage. Column 1 shows the entry and column 2 shows the billbug damage rating.

TABLE 10

Billbug damage

| Entry | Billbug damage rating |
|---|---|
| AWARD | 1.7 |
| SOLAR ECLIPSE (J-2399) | 1.7 |
| 'Barvette' (BAR VV 0709) | 2 |
| SOMBRERO (CP 76-9068) | 2 |
| ALEXA II (J-2404) | 2.3 |
| EVERGLADE | 2.3 |
| NU DESTINY | 2.3 |
| PROSPERITY | 2.3 |
| DIVA | 2.7 |
| EXCURSION | 2.7 |
| JULIA | 2.7 |
| AMERICA | 3 |
| EMBLEM (PST-Y2K-169) | 3 |
| NUCHICAGO (J-1466) | 3 |
| RUGBY II | 3 |
| AURA (A99-2559) | 3.7 |
| BARON | 3.7 |
| WASHINGTON II (RAD-343) | 4 |
| JUMP START (PST-109-752) | 4.3 |
| MIDNIGHT | 4.3 |
| MYSTERE | 4.3 |
| SKYE | 4.3 |
| GREENTEAM (CPP 821) | 4.7 |
| KENBLUE | 5 |
| WASHINGTON | 5 |
| SHAMROCK | 5.3 |
| BANDERA (SPTR 2LM95) | 6.3 |
| REVEILLE | 7 |
| Highest Rated Entry | 1.3 |
| Lowest Rated Entry | 7 |
| LSD VALUE | 2.8 |
| C.V. (%) | 30.9 |

As shown in Table 10, 'Barvette' exhibits a billbug damage rating of 2, indicating that 11 to 19% of area was damaged by billbugs, which is one of the top ratings in the trial. The results demonstrate that 'Barvette' is tolerant to billbug damage.

Table 11 shows the 2010 data for white grub damage of 'Barvette' compared to other Kentucky bluegrass cultivars in the 2005 NTEP trials from turf grown in Knoxville, Tenn. The trial was established in 2005 and consisted of 110 entries. White grub damage is expressed as a percent of the area damaged. Column 1 shows the entry, columns 2 and 3 show the percent damage in July and August, respectively, and column 4 shows the mean percent damage.

TABLE 11

White grub damage

| Entry | White grub damage (%) | | |
|---|---|---|---|
| | July | August | Mean |
| 'Barvette' (BAR VV 0709) | 25 | 21 | 23 |
| EVERGLADE | 23.3 | 37.7 | 30.5 |
| NU DESTINY | 25.7 | 37.7 | 31.7 |
| ALEXA II (J-2404) | 23.3 | 40 | 31.7 |
| AWARD | 25.7 | 40 | 32.8 |
| MYSTERE | 35 | 35 | 35 |
| MIDNIGHT | 31.7 | 40 | 35.8 |
| NUCHICAGO (J-1466) | 30 | 48.3 | 39.2 |
| SOLAR ECLIPSE (J-2399) | 34.3 | 45.7 | 40 |
| KENBLUE | 33.3 | 49 | 41.2 |
| EXCURSION | 29 | 54 | 41.5 |
| REVEILLE | 37.3 | 56.7 | 47 |
| JUMP START (PST-109-752) | 38.3 | 56.7 | 47.5 |
| JULIA | 43.3 | 53.3 | 48.3 |
| BANDERA (SPTR 2LM95) | 41.7 | 56.7 | 49.2 |
| RUGBY II | 45 | 61.7 | 53.3 |
| SKYE | 41.7 | 67.7 | 54.7 |
| BARON | 45 | 68.3 | 56.7 |
| AMERICA | 50 | 70 | 60 |
| AURA (A99-2559) | 55 | 68.3 | 61.7 |
| SHAMROCK | 51.7 | 73.3 | 62.5 |
| PROSPERITY | 50 | 75 | 62.5 |
| SOMBRERO (CP 76-9068) | 53.3 | 72.3 | 62.8 |
| EMBLEM (PST-Y2K-169) | 58.3 | 69 | 63.7 |
| WASHINGTON II (RAD-343) | 60 | 68.3 | 64.2 |
| GREENTEAM (CPP 821) | 51.7 | 79 | 65.3 |
| WASHINGTON | 68.3 | 79.7 | 74 |
| DIVA | 71.7 | 80.7 | 76.2 |
| Highest Rated Entry | 23.2 | 21 | 23 |
| Lowest Rated Entry | 78.3 | 93 | 85.7 |
| LSD VALUE | 23.2 | 25.4 | 22.3 |
| C.V. (%) | 28.6 | 22.9 | 23.7 |

As shown in Table 11, 'Barvette' was the highest rated entry for white grub damage, with the lowest mean percent white grub damage of 23%, demonstrating that 'Barvette' has increased white grub tolerance.

Table 12 shows the 2006-2010 data for stem rust resistance of 'Barvette' compared to other selected Kentucky bluegrass cultivars in the 2005 NTEP trials from turf grown in St. Paul, Minn. (MN) and Stillwater, Okla. (OK). The trial was established in 2005 and consisted of 110 entries. The stem rust damage data estimates the percent of area with stem rust damage using a 1 to 9 rating scale with a score of 0 indicating no damage, a score of 1 indicates 1-10% of area with stem rust damage, a score of 2 indicates 11-19% of area with stem rust damage, a score of 3 indicates 20-39% of area with stem rust damage, a score of 4 indicates 40-49% of area with stem rust damage, a score of 5 indicates 50-59% of area with stem rust damage, a score of 6 indicates 60-69% of area with stem rust damage, a score of 7 indicates 70-79% of area with stem rust damage, a score of 8 indicates 80-89% of area with stem rust damage, and a score of 9 indicates greater than 90% of area with stem rust damage. Column 1 shows the entry and column 2 shows the stem rust damage rating.

TABLE 12

Stem rust damage

| Entry | Stem rust rating | |
|---|---|---|
| | MN | OK |
| 'Barvette' (BAR VV 0709) | 1.7 | 0.8 |
| REVEILLE | 1.3 | 2.3 |
| SKYE | 2.3 | 2.3 |
| WASHINGTON | 3 | 2.3 |
| WASHINGTON II (RAD-343) | 1.3 | 2.7 |
| ALEXA II (J-2404) | 6.3 | 2.8 |
| EXCURSION | 5.3 | 2.9 |
| MYSTERE | 2.7 | 2.9 |
| NUCHICAGO (J-1466) | 4.7 | 2.9 |
| SOMBRERO (CP 76-9068) | 7.7 | 2.9 |
| AURA (A99-2559) | 2.7 | 3 |
| DIVA | 2 | 3 |
| KENBLUE | 3 | 3 |
| RUGBY II | 5 | 3 |
| AWARD | 5.7 | 3.1 |
| NU DESTINY | 5 | 3.1 |
| EVERGLADE | 4.7 | 3.2 |
| SOLAR ECLIPSE (J-2399) | 6 | 3.2 |
| BARON | 4.3 | 3.3 |
| MIDNIGHT | 4 | 3.3 |
| AMERICA | 4 | 3.4 |
| GREENTEAM (CPP 821) | 6.7 | 3.4 |
| JULIA | 5 | 3.7 |
| PROSPERITY | 5.7 | 3.8 |
| SHAMROCK | 4 | 3.8 |
| BANDERA (SPTR 2LM95) | 2.7 | 4.1 |
| EMBLEM (PST-Y2K-169) | 5.7 | 4.6 |
| JUMP START (PST-109-752) | 5.7 | 5 |
| Highest Rated Entry | 1.3 | 0.8 |
| Lowest Rated Entry | 7.7 | 5 |
| LSD VALUE | 1.7 | 1.5 |
| C.V. (%) | 20.7 | 17.3 |

As shown in Table 12, 'Barvette' has the second highest rating in MN and the highest rating in the OK trial, with less than 1% of the area suffering from stem rust, demonstrating that 'Barvette' is resistant to stem rust.

In general, Kentucky bluegrass is a cool season grass that is intolerant of summer stresses, such as drought and heat. Conversely, Kentucky bluegrass variety 'Barvette' is better able to tolerate summer stresses by having superior turfgrass quality ratings, higher percentage of living ground cover, and forming a more dense summer canopy than other Kentucky bluegrass varieties. Table 13 shows the 2010 mean turfgrass quality ratings of 'Barvette' compared to other Kentucky bluegrass varieties in the 2005 NTEP trials from turf grown at six locations in the Transition Zone of the United States, including Lexington, Ky., College Park, Md., Raleigh, N.C., Stillwater, Okla., Knoxville, Tenn., and Blacksburg, Va. The trial was established in 2005 and consisted of 110 entries. The turf quality ratings are given in a 1 to 9 scale, with 9 indicating the best turf. Column 1 shows the entry, column 2 shows the quality ratings at the Kentucky site (KY), column 3 shows the quality ratings at the Maryland site (MD), column 4 shows the quality ratings at the North Carolina site (NC), column 5 shows the quality ratings at the Oklahoma site (OK), column 6 shows the quality ratings at the Tennessee site (TN), column 7 shows the quality ratings at the Virginia site (VA), and column 8 shows the mean quality ratings for all sites.

TABLE 13

Summer performance turfgrass quality ratings

| Entry | Turfgrass quality ratings | | | | | | |
|---|---|---|---|---|---|---|---|
| | KY | MD | NC | OK | TN | VA | Mean |
| 'Barvette' (BAR VV 0709) | 6 | 6 | 8 | 7.3 | 6.1 | 6.2 | 6.6 |
| ALEXA II (J-2404) | 6.9 | 7.5 | 6.7 | 6 | 6 | 5.5 | 6.4 |
| NUCHICAGO (J-1466) | 7.3 | 6.8 | 7 | 6.1 | 6 | 5.4 | 6.4 |
| MIDNIGHT | 7.1 | 6.9 | 6.2 | 6.3 | 5.7 | 5.4 | 6.3 |
| AWARD | 6.8 | 7 | 6.6 | 5.4 | 6 | 5.6 | 6.2 |
| EVERGLADE | 7.2 | 6.6 | 5.4 | 6 | 6.2 | 5.6 | 6.2 |
| NU DESTINY | 7.1 | 7.2 | 6.1 | 5 | 6.2 | 5.7 | 6.2 |
| SOLAR ECLIPSE (J-2399) | 7.3 | 7.4 | 6.3 | 5.6 | 5.7 | 5.1 | 6.2 |
| EXCURSION | 6.9 | 7.1 | 6.4 | 5 | 5.8 | 5.3 | 6.1 |
| MYSTERE | 6.7 | 5.7 | 5.8 | 5.9 | 6.4 | 5.7 | 6 |
| AURA (A99-2559) | 7 | 6.6 | 5.2 | 5.1 | 5.5 | 6.4 | 5.9 |
| RUGBY II | 6.7 | 6.3 | 6.3 | 5.4 | 5.5 | 5.5 | 5.9 |
| SKYE | 6.4 | 5.3 | 6.4 | 4.3 | 5.4 | 5.4 | 5.5 |
| WASHINGTON | 6.1 | 5.9 | 6.5 | 4.8 | 4.9 | 4.8 | 5.5 |
| DIVA | 6.4 | 6.1 | 5.7 | 4.2 | 4.7 | 5.1 | 5.4 |
| PROSPERITY | 6.6 | 4.5 | 5 | 5.2 | 5.3 | 5.1 | 5.3 |
| JUMP START (PST-109-752) | 5.6 | 5.8 | 5.4 | 4 | 6 | 4.4 | 5.2 |
| REVEILLE | 5.5 | 4.3 | 6.8 | 4.7 | 5.7 | 4.5 | 5.2 |
| AMERICA | 6.1 | 4.6 | 5.3 | 4.5 | 5.2 | 4.9 | 5.1 |
| BARON | 5.3 | 6 | 4.9 | 5.2 | 5 | 4.6 | 5.1 |
| SHAMROCK | 5.1 | 6 | 4.9 | 4.7 | 5.1 | 4.9 | 5.1 |
| EMBLEM (PST-Y2K-169) | 6 | 6.8 | 4 | 3.9 | 5.2 | 4.1 | 5 |
| WASHINGTON II (RAD-343) | 5.7 | 4.4 | 5.7 | 4.3 | 4.9 | 5 | 5 |
| KENBLUE | 4.9 | 4.7 | 3.9 | 5.3 | 5.3 | 5.5 | 4.9 |
| BANDERA (SPTR 2LM95) | 4.7 | 4.7 | 5.5 | 4.9 | 5 | 4.3 | 4.8 |
| GREENTEAM (CPP 821) | 5 | 4.4 | 4.1 | 4 | 5.5 | 4.3 | 4.6 |
| JULIA | 4.6 | 4.6 | 2.9 | 4.3 | 5.7 | 4.8 | 4.5 |
| SOMBRERO (CP 76-9068) | 5.3 | 3.2 | 3.2 | 4 | 5.5 | 4.4 | 4.3 |
| Highest Rated Entry | 7.7 | 7.7 | 8 | 7.3 | 6.1 | 6.2 | 6.6 |
| Lowest Rated Entry | 3.6 | 3.2 | 2.9 | 3.4 | 4.3 | 4.1 | 4.3 |
| LSD VALUE | 1 | 1.1 | 2.1 | 1.7 | 0.7 | 0.9 | 0.5 |
| C.V. (%) | 9.9 | 11.6 | 24.9 | 22.9 | 7.8 | 10.5 | 15.5 |

As shown in Table 13, 'Barvette' was the top rated bluegrass for turfgrass quality with a mean rating of 6.6, demonstrating that 'Barvette' has increased tolerance to summer stresses.

Table 14 shows the 2006-2010 summer ratings of percent living ground cover of 'Barvette' compared to other Kentucky bluegrass varieties and selections in the 2005 NTEP trials from turf grown at four locations in the United States, including Lexington, Ky., Stillwater, Okla., Knoxville, Tenn., and Blacksburg, Va. The trial was established in 2005 and consisted of 110 entries. The ratings of percent living ground cover are given in a 1 to 100% scale, with 100% indicating all living ground cover in an area. Column 1 shows the entry, column 2 shows the percent living cover at the Kentucky site (KY), column 3 shows the percent living cover at the Oklahoma site (OK), column 4 shows the percent living cover at the Tennessee site (TN), column 5 shows the percent living cover at the Virginia site (VA), and column 6 shows the mean percent living cover for all sites.

TABLE 14

Summer ratings of living ground cover

| Entry | Percent living ground cover | | | | |
|---|---|---|---|---|---|
| | KY | OK | TN | VA | Mean |
| 'Barvette' (BAR VV 0709) | 98.7 | 96.1 | 88.5 | 96.3 | 94.9 |
| MIDNIGHT | 99 | 77.9 | 87.5 | 99 | 90.9 |
| NUCHICAGO (J-1466) | 99 | 77.7 | 88.2 | 97.7 | 90.7 |
| ALEXA II (J-2404) | 99 | 77 | 89.5 | 93 | 89.6 |
| DIVA | 99 | 77.1 | 80.9 | 96.3 | 88.3 |
| EXCURSION | 96 | 74.3 | 87.5 | 95 | 88.2 |
| WASHINGTON | 86.3 | 76.7 | 80.3 | 99 | 85.6 |
| AWARD | 99 | 78.7 | 87.6 | 96 | 90.3 |
| NU DESTINY | 99 | 76.7 | 89.7 | 94.7 | 90.0 |
| SOMBRERO (CP 76-9068) | 96 | 71.5 | 82.1 | 92.7 | 85.6 |
| EVERGLADE | 94 | 78.9 | 89.5 | 97.7 | 90.0 |
| AURA (A99-2559) | 86.3 | 86 | 82.8 | 97.7 | 88.2 |
| SKYE | 86.3 | 82.5 | 85 | 99 | 88.2 |
| RUGBY II | 99 | 83 | 83.3 | 96 | 90.3 |
| PROSPERITY | 94.3 | 67.7 | 81.3 | 92.7 | 84.0 |
| WASHINGTON II (RAD-343) | 89.3 | 67.7 | 79.1 | 99 | 83.8 |
| GREENTEAM (CPP 821) | 93.7 | 59.9 | 82.3 | 96.3 | 83.1 |
| MYSTERE | 86 | 78.1 | 86.9 | 99 | 87.5 |
| AMERICA | 89.3 | 67.3 | 84.5 | 97.7 | 84.7 |
| SOLAR ECLIPSE (J-2399) | 99 | 68.8 | 86.8 | 99 | 88.4 |
| JULIA | 83.3 | 68 | 83.1 | 99 | 83.4 |
| BANDERA (SPTR 2LM95) | 69.7 | 69.5 | 84.8 | 93 | 79.3 |
| JUMP START (PST-109-752) | 81.7 | 68.7 | 83.4 | 99 | 83.2 |
| BARON | 75 | 53.2 | 84 | 99 | 77.8 |
| KENBLUE | 36.7 | 73.9 | 83.6 | 95 | 72.3 |
| REVEILLE | 43.3 | 71.9 | 86.4 | 89.3 | 72.7 |
| SHAMROCK | 83 | 49 | 82.5 | 96 | 77.6 |
| Highest Rated Entry | 99 | 96.1 | 88.5 | 99 | 95.7 |
| Lowest Rated Entry | 25.7 | 49 | 74.3 | 89.3 | 59.6 |
| LSD VALUE | 17.6 | 32.6 | 9.2 | 8 | |
| C.V. (%) | 12.4 | 30.1 | 8.4 | 5.2 | |

As shown in Table 14, 'Barvette' was the highest rated entry for summer ratings of percent living ground cover with a mean percent living ground cover of 94.9% across all sites, demonstrating that 'Barvette' has increased tolerance to summer stresses.

Table 15 shows the 2010 summer ratings of percent living ground cover of 'Barvette' compared to other Kentucky bluegrass varieties and selections in the 2005 NTEP trials from turf grown at Stillwater, Okla. and Knoxville, Tenn. The trial was established in 2005 and consisted of 110 entries. The ratings of percent living ground cover are given in a 1 to 100% scale, with 100% indicating all living ground cover in an area. Column 1 shows the entry, column 2 shows the percent living cover at the Oklahoma site (OK), column 3 shows the percent living cover at the Tennessee site (TN), and column 4 shows the mean percent living cover for all sites.

TABLE 15

Summer ratings of living ground cover

| Entry | Percent living ground cover | | |
|---|---|---|---|
| | OK | TN | Mean |
| 'Barvette' (BAR VV 0709) | 99 | 75 | 87.0 |
| ALEXA II (J-2404) | 83.3 | 76.7 | 80.0 |
| AWARD | 83.3 | 74.3 | 78.8 |
| NU DESTINY | 82.7 | 74.3 | 78.5 |
| MIDNIGHT | 86 | 68.3 | 77.2 |
| RUGBY II | 93.3 | 55 | 74.2 |
| SOLAR ECLIPSE (J-2399) | 81.7 | 65.7 | 73.7 |
| BANDERA (SPTR 2LM95) | 81 | 58.3 | 69.7 |
| SKYE | 80 | 58.3 | 69.2 |
| EVERGLADE | 58.3 | 76.7 | 67.5 |

TABLE 15-continued

Summer ratings of living ground cover

| Entry | Percent living ground cover | | |
|---|---|---|---|
| | OK | TN | Mean |
| EXCURSION | 61.7 | 71 | 66.4 |
| KENBLUE | 64.3 | 66.7 | 65.5 |
| NUCHICAGO (J-1466) | 58.3 | 70 | 64.2 |
| AURA (A99-2559) | 81.7 | 45 | 63.4 |
| JUMP START (PST-109-752) | 63.3 | 61.7 | 62.5 |
| AMERICA | 70 | 50 | 60.0 |
| PROSPERITY | 68.3 | 50 | 59.2 |
| SOMBRERO (CP 76-9068) | 71 | 46.7 | 58.9 |
| JULIA | 60 | 56.7 | 58.4 |
| MYSTERE | 51 | 65 | 58.0 |
| WASHINGTON | 83.3 | 31.7 | 57.5 |
| GREENTEAM (CPP 821) | 64.3 | 48.3 | 56.3 |
| BARON | 56 | 55 | 55.5 |
| SHAMROCK | 58.3 | 48.3 | 53.3 |
| EMBLEM (PST-Y2K-169) | 60 | 41.7 | 50.9 |
| REVEILLE | 38.3 | 62.7 | 50.5 |
| DIVA | 70 | 28.3 | 49.2 |
| WASHINGTON II (RAD-343) | 56.7 | 40 | 48.4 |
| Highest Rated Entry | 99 | 75 | 87.0 |
| Lowest Rated Entry | 5 | 21.7 | 19.2 |
| LSD VALUE | 46.7 | 21.8 | |
| C.V. (%) | 46.7 | 25.3 | |

As shown in Table 15, 'Barvette' was the highest rated entry for summer ratings of percent living ground cover with a mean percent living ground cover of 87.0% across all sites, demonstrating that 'Barvette' has increased tolerance to summer stresses.

Table 16 shows the 2010 data for summer canopy density ratings of 'Barvette' compared to other Kentucky bluegrass varieties in the 2005 NTEP trials from turf grown at Raleigh, N.C. The trial was established in 2005. The summer canopy density data estimates the percent of area with summer canopy density using a 1 to 9 rating scale with a score of 0 indicating no density, a score of 1 indicates 1-10% of area with summer canopy density, a score of 2 indicates 11-19% of area with summer canopy density, a score of 3 indicates 20-39% of area with summer canopy density, a score of 4 indicates 40-49% of area with summer canopy density, a score of 5 indicates 50-59% of area with summer canopy density, a score of 6 indicates 60-69% of area with summer canopy density, a score of 7 indicates 70-79% of area with summer canopy density, a score of 8 indicates 80-89% of area with summer canopy density, and a score of 9 indicates greater than 90% of area with summer canopy density. Column 1 shows the entry and column 2 shows the summer canopy density rating at the North Carolina site (NC).

TABLE 16

Summer canopy density

| Entry | Summer canopy density rating |
|---|---|
| 'Barvette' (BAR VV 0709) | 9 |
| NUCHICAGO (J-1466) | 7.3 |
| REVEILLE | 6.7 |
| AWARD | 6.3 |
| SKYE | 6 |
| WASHINGTON | 6 |
| ALEXA II (J-2404) | 5.7 |

TABLE 16-continued

Summer canopy density

| Entry | Summer canopy density rating |
|---|---|
| EXCURSION | 5.7 |
| JUMP START (PST-109-752) | 5.7 |
| NU DESTINY | 5.7 |
| BANDERA (SPTR 2LM95) | 5.3 |
| GREENTEAM (CPP 821) | 5.3 |
| MIDNIGHT | 5.3 |
| MYSTERE | 5.3 |
| RUGBY II | 5.3 |
| SOLAR ECLIPSE (J-2399) | 5.3 |
| WASHINGTON II (RAD-343) | 5.3 |
| AMERICA | 5 |
| DIVA | 5 |
| EVERGLADE | 4.7 |
| KENBLUE | 4.7 |
| PROSPERITY | 4.7 |
| SHAMROCK | 4.7 |
| AURA (A99-2559) | 4.3 |
| BARON | 4.3 |
| SOMBRERO (CP 76-9068) | 3.7 |
| EMBLEM (PST-Y2K-169) | 2.7 |
| JULIA | 2.3 |
| Highest Rated Entry | 9 |
| Lowest Rated Entry | 1.7 |
| LSD VALUE | 3.1 |
| C.V. (%) | 39.9 |

As shown in Table 16, 'Barvette' was the highest rated entry for summer canopy density with a rating of 9, indicating greater than 90% of the area with canopy density and further demonstrating that 'Barvette' has increased tolerance to summer stresses.

Tables 17a-17e show the results of SSR marker genotyping for Kentucky bluegrass variety 'Barvette' compared to commercial and experimental varieties of Kentucky bluegrass; samples Bararri, Barimpala and Baron are Barenbrug varieties, and samples Midnight, Brooklawn and Kenblue are standards. Forty-five *Poa pratensis* SSRs were screened on all bluegrass samples using a modified DLM SSR protocol on the ABI 3730XL capillary electrophoresis system. The genotyping results were scored using the GeneMapper software V4.0. The failed samples were repeated at least once. The results show the size in base pairs of amplified loci and alleles at specific marker sites for *Poa pratensis*. The base pair size of each marker amplification product generates a particular genomic fingerprint specific to each cultivar. When compared to 'Barvette', any off-types would be identified by any marker not exhibiting the same results as seen for 'Barvette'. A "failed" designation indicates a null locus, for example, a "failed" result for 'Barvette' means that a locus present in the other lines giving a base pair result is absent in 'Barvette', such as for Poa51.

TABLE 17a

SSR Genotyping results

| Sample | Poa51 | Poa69 | Poa70 | Poa72 | Poa73 | Poa76 | Poa77 | Poa78 |
|---|---|---|---|---|---|---|---|---|
| Bararri | 113 | 149/161 | 133 | 195/215 | 170/173/177 | 188 | Failed | 138/140/160/166/168 |
| Barimpala | 113 | 151 | 133/151/157/165 | 186/192/195/201 | 170/173/177 | 180 | 176/308 | 140/160/166/168 |
| Baron | 113/248 | 149/151/161 | 99/133 | 192/195/239 | 170/173/177 | 188 | Failed | 140/160/166/168/176 |
| 'Barvette' | Failed | 149/151/161 | Failed | 201 | 173/177 | 188 | 108/176 | 140/144/160 |
| Brooklawn | 113 | 141/147/149/151 | 99/133 | 189/195/215 | 170/173/177 | 180/188 | 176 | 160/168 |
| Kenblue | 113/189/365 | 149/151 | 99/133 | 179/195 | 170/173/175/177 | 180/188 | 168/176/368 | 140/144/148/160 |
| Midnight | 113 | 149/151 | 99/125/133 | 112/195/201 | 170/173/177 | 180/188 | 176 | 140/160/166/176 |

TABLE 17b

SSR Genotyping results

| Sample | Poa98 | Poa131 | Poa213 | Poa217 | Poa218 | Poa221 | Poa222 | Poa223 | Poa224 | Poa225 |
|---|---|---|---|---|---|---|---|---|---|---|
| Bararri | Failed | Failed | 125/134 | 106/249 | 91/112/167/174 | 142 | 149 | 107/109/112/116/118 | 106 | 238 |
| Barimpala | Failed | Failed | 134 | 179/188/249 | 91/112/150/174 | 142/152 | 149 | 104/114/151 | 106 | 353 |
| Baron | Failed | Failed | 125/134/146 | 192/249 | 91/112/158/174 | 142/144/148/152/164 | 149 | 91/116 | 106 | 238 |
| 'Barvette' | Failed | Failed | 125 | Failed | 91 | 142 | 149 | 109/116 | 106 | 353 |
| Brooklawn | Failed | Failed | 134 | 249 | 112/167/174 | 142/148 | 149 | 104/109 | 106 | 175 |
| Kenblue | Failed | Failed | 134 | 188/249 | 146 | 142/144/152/164 | 149 | 104/107/109/112/116/146 | 106 | 353 |
| Midnight | Failed | Failed | 134/216 | 192/249 | 112/133 | 142/144/152/164 | 149 | 109/116 | 106 | Failed |

TABLE 17c

SSR Genotyping results

| Sample | Poa226 | Poa229 | Poa230 | Poa231 | Poa232 | Poa287 | Poa288 | Poa 289 | Poa290 |
|---|---|---|---|---|---|---|---|---|---|
| Bararri | 85/95/100/193/228/263/338 | 158 | 85/122/156 | 250 | 159 | Failed | 381/383/393/403/415 | 252/269/272 | 260/265/271/284 |
| Barimpala | 177 | 158 | 85/122/156 | Failed | 159 | Failed | 381/385/393/417 | 252/272 | 260/271/276/284 |
| Baron | 190/193/254/338 | 158 | 85/122/156 | Failed | 151/159 | Failed | Failed | 252/269/272 | 271/274/284 |
| 'Barvette' | 100/263 | 158 | 85/122/156 | 250 | 159 | Failed | 381/385 | 252/266/272 | 260/271/278/280/282 |
| Brooklawn | 100/263 | 158 | 85/122/156 | 250 | 159 | Failed | 368/381/391/393/397 | 252/272 | 260/271/274/284 |
| Kenblue | 177 | 158 | 85/122/156 | Failed | 159 | Failed | 381 | 252/272 | 260/271/276/278/280 |
| Midnight | 100/190/263/338 | 158 | 85/122/156 | 250 | 159 | Failed | 381/393/401 | 252/272 | 260/271/274 |

TABLE 17d

SSR Genotyping results

| Sample | Poa292 | Poa293 | Poa 294 | Poa 295 | Poa299 | Poa310 | Poa317 | Poa318 | Poa319 | Poa322 | Poa323 |
|---|---|---|---|---|---|---|---|---|---|---|---|
| Bararri | Failed | Failed | 177/435 | 425 | 215 | Failed | 100 | Failed | 414/417/425 | 195 | 444 |
| Barimpala | 209/230 | Failed | 177 | 402/422/425 | 215 | Failed | 100 | 99/108 | 410/414/419/425 | 195 | Failed |
| Baron | 202/230/239 | Failed | 162/177/228/245 | 402/422/425 | 215 | Failed | 100 | 99 | 414/425 | 195 | 444 |
| 'Barvette' | 200/239 | Failed | Failed | 402/422/425 | 215 | Failed | 100 | 99 | Failed | 195 | 444 |
| Brooklawn | Failed | Failed | Failed | 402/425 | 215 | Failed | 100 | 101/108 | 414 | 195 | 444 |
| Kenblue | 202/230/234/239 | Failed | Failed | 402/422/425 | 215 | Failed | 100 | 99/101/108 | 410/414/417/425 | 195 | 444 |
| Midnight | Failed | Failed | 107/177/228/337 | 402/422/425 | 215 | Failed | 100 | 99/101 | 412/414/417/425 | 195 | 444 |

TABLE 17e

SSR Genotyping results

| Sample | Poa324 | Poa326 | Poa327 | Poa328 | Poa332 | Poa333 | Poa336 |
|---|---|---|---|---|---|---|---|
| Bararri | 418 | 136/180 | 253/262/265 | 420/422/428 | 174 | 264 | 353/361 |
| Barimpala | 418 | 142/180 | 262/265/267/270 | 422/428 | 162/174 | Failed | 113/353/361 |
| Baron | 418 | 142/180 | 253/262/265/270 | 422/428 | 138/174 | Failed | 361 |
| 'Barvette' | 418 | 132/136 | 262/265/267/270 | 422/428 | 170/174 | Failed | 113/140/353/361 |
| Brooklawn | 418 | 136/162/180 | 253/262/265 | 420/428 | 174 | 264 | 100/361 |

TABLE 17e-continued

SSR Genotyping results

| Sample | Poa324 | Poa326 | Poa327 | Poa328 | Poa332 | Poa333 | Poa336 |
|---|---|---|---|---|---|---|---|
| Kenblue | 401/404/409/418 | 136/162/180 | 253/262/265/270 | 428 | 94/102/138/174/241 | 264 | 361 |
| Midnight | 418 | 132/180 | 253/262/265 | 422/428 | 107/138/174 | 264/269 | 353/361 |

As shown in Tables 17a-17e, the SSR genotyping generated a very specific and unique marker genotype for 'Barvette'. 'Barvette' is different from all other samples tested at 14 of the 45 SSR markers; specifically, 'Barvette' is unique at markers Poa51, Poa72, Poa73, Poa77, Poa78, Poa217, Poa218, Poa288, Poa289, Poa290, Poa292, Poa326, Poa332 and Poa336. The results shown in Tables 17a-17e indicate that 'Barvette' is a unique and novel variety of Kentucky bluegrass.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the Barenbrug USA, Inc. proprietary Kentucky bluegrass seed designated 'Barvette' containing mutant allele BARHGTMA1 of the present invention, disclosed above and recited in the appended claims has been made with the National Collections of Industrial, Food and Marine Bacteria (NCIMB), 23 St Machar Drive, Aberdeen, Scotland, AB24 3RY, United Kingdom. The date of deposit was Jan. 23, 2013. The deposit of 2,500 seeds was taken from the same deposit maintained by Barenbrug USA, Inc. since prior to the filing date of this application. Upon allowance of any claims in this application, all restrictions on the availability to the public of the variety will be irrevocably removed by affording access to a deposit of at least 2,500 seeds of the same variety with the National Collections of Industrial, Food and Marine Bacteria (NCIMB), Aberdeen, Scotland, and the deposit is intended to meet all of the requirements of 37 C.F.R. 1.801-1.809. The NCIMB number is 42095. The deposit will be maintained in the depository for a period of 30 years, or 5 years after the last request, or for the effective life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of Kentucky bluegrass variety 'Barvette', wherein a representative sample seed of said variety is deposited under NCIMB number 42095.

2. A Kentucky bluegrass plant, or a part thereof, produced by growing the seed of claim 1.

3. A Kentucky bluegrass plant designated 'Barvette', wherein a representative sample seed of said plant is deposited under NCIMB number 42095, wherein said plant has a combination of resistance to Summer Patch caused by the fungus *Magnaporthe poae*, traffic tolerance and increased traffic recovery.

4. The Kentucky bluegrass plant of claim 3, further comprising one or more characteristics selected from the group consisting of increased tolerance to billbug damage, increased tolerance to white grub damage, increased tolerance to summer stresses, and resistance to stem rust.

5. A tissue culture of cells produced from the bluegrass plant of claim 3, wherein said cells of tissue culture are produced from a plant part selected from the group consisting of embryos, meristematic cells, leaf, pollen, cotyledon, hypocotyl, root, root tip, pistil, anther, flower, shoot, stem, and leaf sheath.

6. A bluegrass plant regenerated from the tissue culture of claim 5, wherein the plant has the morphological and physiological characteristics of Kentucky bluegrass variety 'Barvette'.

7. Progeny of the plant of claim 3, said progeny having all of the physiological and morphological characteristics of Kentucky bluegrass variety 'Barvette'.

8. A sod, comprising the grass plant of claim 3.

9. The grass plant of claim 3, wherein said grass is planted in a lawn.

10. A vegetative sprig or clone of the grass plant of claim 3.

11. A bluegrass plant produced by introducing a transgene into the plant of claim 3 by backcrossing or genetic transformation.

12. A method for producing a bluegrass seed, comprising crossing two bluegrass plants and harvesting the resultant bluegrass seed, wherein at least one bluegrass plant is the bluegrass plant of claim 3.

13. An $F_1$ bluegrass seed produced by the method of claim 12.

14. An $F_1$ bluegrass plant, or a part thereof, produced by growing said seed of claim 13.

15. The method of claim 12, wherein at least one of said bluegrass plants is transgenic.

16. A method of producing an herbicide resistant bluegrass plant, wherein said method comprises introducing a gene conferring herbicide resistance into the plant of claim 3.

17. A herbicide resistant bluegrass plant produced by the method of claim 16, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, aryloxyphenoxy propionate, and benzonitrile.

18. A method of producing a pest or insect resistant bluegrass plant, wherein said method comprises introducing a gene conferring pest or insect resistance into the bluegrass plant of claim 3.

19. A pest or insect resistant bluegrass plant produced by the method of claim 18.

20. The bluegrass plant of claim 19, wherein the gene encodes a *Bacillus thuringiensis* (Bt) endotoxin.

21. A method of producing a disease resistant bluegrass plant, wherein said method comprises introducing a gene which confers disease resistance into the bluegrass plant of claim 3.

22. A disease resistant bluegrass plant produced by the method of claim 21.

23. A method of introducing a desired trait into Kentucky bluegrass variety 'Barvette', wherein the method comprises:
  a. crossing a 'Barvette' plant, wherein a representative sample of seed is deposited under NCIMB number 42095, with a plant selected from the group consisting of another bluegrass variety, another species of *Poa*, and another plant genus that comprises a desired trait to produce progeny plants;
  b. selecting one or more progeny plants that have the desired trait to produce selected progeny plants;
  c. backcrossing the selected progeny plants with Kentucky bluegrass variety 'Barvette' to produce backcross progeny plants;
  d. selecting for backcross progeny plants that have the desired trait; and
  e. repeating steps c and d two or more times in succession to produce selected third or higher backcross progeny plants that comprise the desired trait.

24. The method of claim 23, wherein the desired trait is a phenotypic trait, a gene, or a molecular marker.

25. A Kentucky bluegrass plant produced by the method of claim 24, wherein the plant has the desired trait and otherwise all of the physiological and morphological characteristics of Kentucky bluegrass variety 'Barvette'.

* * * * *